(12) United States Patent
Momoda et al.

(10) Patent No.: US 6,340,765 B1
(45) Date of Patent: Jan. 22, 2002

(54) CHROMENE COMPOUND

(75) Inventors: Junji Momoda; Yuichiro Kawabata, both of Tokuyama (JP)

(73) Assignee: Tokuyama Corporation, Yamaguchi-Ken (JP)

(*) Notice: Subject to any disclaimer, the term of this patent is extended or adjusted under 35 U.S.C. 154(b) by 0 days.

(21) Appl. No.: 09/572,896

(22) Filed: May 18, 2000

(30) Foreign Application Priority Data

May 20, 1999 (JP) ............................................. 11-140836
Oct. 26, 1999 (JP) ............................................. 11-303967

(51) Int. Cl.⁷ ............................................. C07D 311/96
(52) U.S. Cl. ........................ 549/330; 549/331; 544/150; 546/15; 548/407; 252/586; 523/135; 524/110
(58) Field of Search ................................. 549/331, 330, 549/150; 546/15; 548/407

(56) References Cited

FOREIGN PATENT DOCUMENTS

DE   19902771   12/1999
WO    9614596    5/1996

*Primary Examiner*—Bernard Dentz

(57) ABSTRACT

A photochromic compound having a high color-developing sensitivity, a large fading rate and good durability of photochromic property. A novel chromene compound is, for example, represented by the following formula,

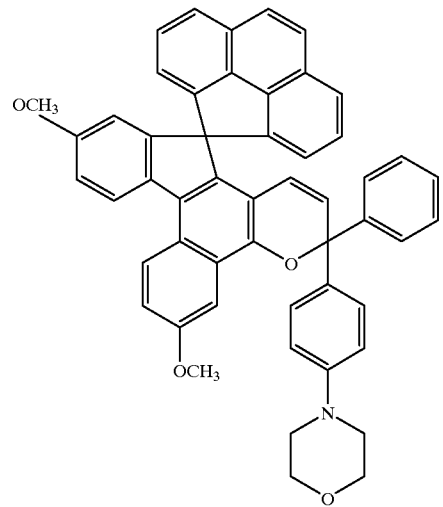

and in which, as a basic structure, a condensed ring having a particular divalent group bonded to carbon atoms at the fourth and fifth positions of a fluoreno group is spiro-bonded to the first position of an indene ring, a particular divalent group is bonded to carbon atoms at the fifth and sixth positions of a chromene ring to form a condensed ring, and particular substituents are bonded to a carbon atom at the second position of the chromene ring.

26 Claims, 1 Drawing Sheet

CHROMENE COMPOUND

BACKGROUND OF THE INVENTION 1. (Field of the Invention)

The present invention relates to a novel chromene compound and to a photochromic polymerizable composition containing the chromene compound. The invention is further related to a photochromic material containing the chromene compound and, particularly, to a photochromic optical material.

2. (Background of the Invention)

Photochromism is a phenomenon that is drawing attention in the past several years, and stands for a reversible action of a compound which quickly changes its color when it is irradiated with light containing ultraviolet rays such as sun light or light from a mercury lamp and resumes its initial color when it is no longer irradiated with light but is placed in a dark place. The compound having this property is called photochromic compound, and various compounds have heretofore been synthesized without, however, any particular common nature in their structures.

International Patent Publication WO96/14596 discloses a chromene compound represented by the following formula (A),

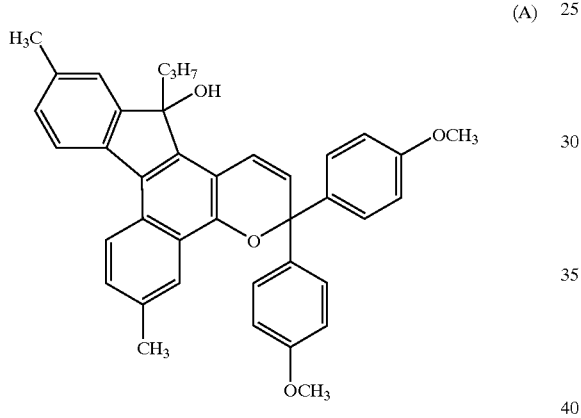

(A)

However, this chromene compound has a low color-developing sensitivity and a low fading rate. When used for extended periods of time as a photochromic material, further, this chromene compound is colored to a large extent (also called coloring after aged) in a state of not being irradiated with light and exhibits a decreased color density when irradiated with light.

Further, International Patent Publication WO97/48762 discloses a chromene compound represented by the following formula (B),

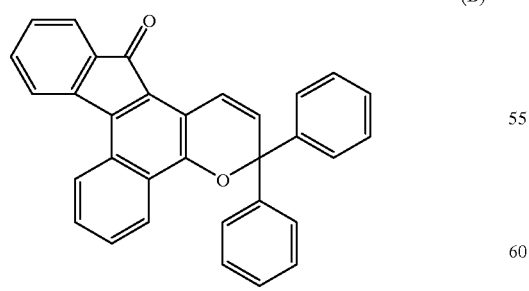

(B)

However, this chromene compound has a problem of a low color fading rate.

Further, German Patent Application Publication DE 19902771 A1 discloses in its Examples 4, 7 and 5 the chromene compounds represented by the following formulas (C), (D) and (E)

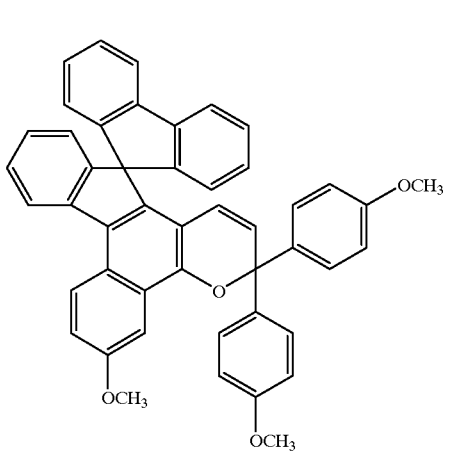

(C)

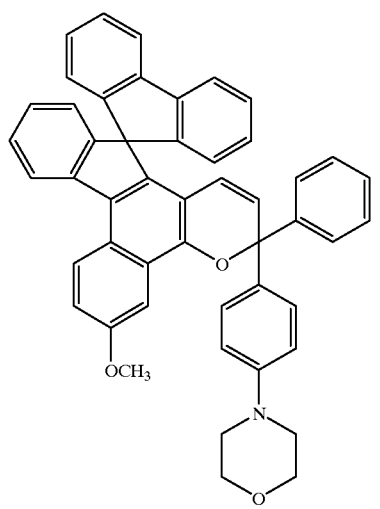

(D)

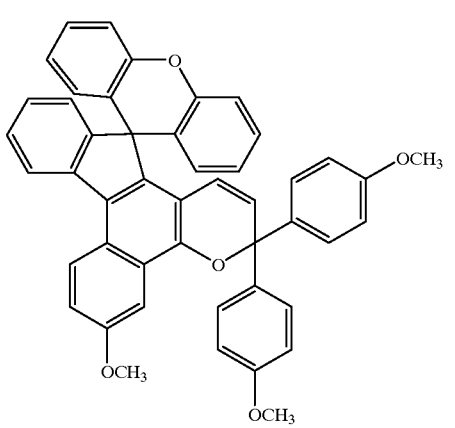

(E)

However, these chromene compounds have such problems that their color-developing sensitivities are low and, besides, their fading rates are not of satisfactory levels.

SUMMARY OF THE INVENTION

The object of the present invention is to provide a chromene compound featuring further improved photochromic properties compared to those of the above-mentioned compounds, exhibiting a high color-developing sensitivity, a high fading rate, being little colored after aged, and permitting the photochromic properties to be little deteriorated, i.e., permitting the color density to drop little, and exhibiting excellent durability of photochromic property.

The present invention was proposed in order to accomplish the above-mentioned object, and was completed based on a knowledge that the novel chromene compound which was obtained by the present inventors exhibits a high color-developing sensitivity, a large fading rate, a small coloring after aged, and excellent durability of photochromic property.

That is, according to the present invention, the chromene compound is represented by the following general formula (1),

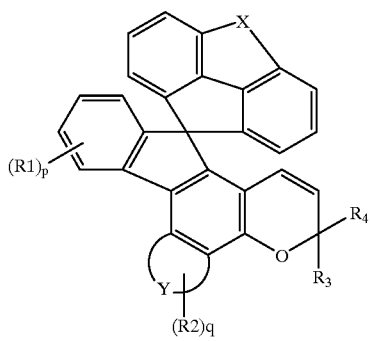

(1)

wherein, $R^1$ is an alkyl group, a hydroxy group, an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the indene ring through the carbon atom, a monovalent substituted or unsubstituted heterocyclic group having a nitrogen atom as a hetero atom and bonded to the indene ring through the nitrogen atom, or a monovalent condensed heterocyclic group in which said heterocyclic group is condensed with an aromatic hydrocarbon ring or an aromatic heterocyclic ring, p is an integer of from 0 to 3;

a divalent group represented by the following formula (2),

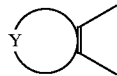

(2)

is an aromatic hydrocarbon group or an unsaturated heterocyclic ring;

$R^2$ is an alkyl group, a hydroxy group, an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the ring of the group represented by the above formula (2) through the carbon atom, a monovalent substituted or unsubstituted heterocyclic group having a nitrogen atom as a hetero atom and is bonded to the ring of the group represented by the above formula (2) through the nitrogen atom, or a monovalent condensed heterocyclic group in which said heterocyclic group is condensed with an aromatic hydrocarbon ring or an aromatic heterocyclic ring, q is an integer of from 0 to 3;

$R^3$ and $R^4$ are, independently from each other, group represented by the following formula (3),

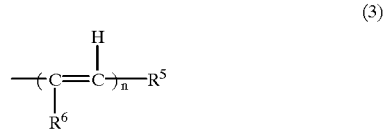

(3)

wherein $R^5$ is a substituted or unsubstituted aryl group, or a substituted or unsubstituted heteroaryl group, $R^6$ is a hydrogen atom, an alkyl group or a halogen atom, and n is an integer of from 1 to 3;

group represented by the following formula (4),

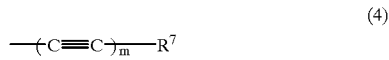

(4)

wherein $R^7$ is a substituted or unsubstituted aryl group, or a substituted or unsubstituted heteroaryl group, and m is an integer of from 1 to 3;

substituted or unsubstituted aryl groups, or substituted or unsubstituted heteroaryl groups, or;

$R^3$ and $R^4$ are group which, in combination, constitute an aliphatic hydrocarbon ring or an aromatic hydrocarbon ring; and X is represented by any one of the following formula,

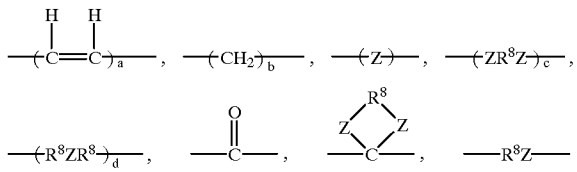

wherein Z is an oxygen atom or a sulfur atom, $R^8$ is an alkylene group with 1 to 6 carbon atoms, and a, b, c and d are integers of from 1 to 4 independently from each other.

As represented by the above-mentioned general formula (1), the chromene compound of the present invention has a basic structure in which:

①  a condensed ring formed by a particular divalent group —X— bonded to the carbon atoms at the fourth and fifth positions of the fluorene ring, is spiro-bonded to the first position of the indene ring;

②  a condensed ring is formed by a divalent group represented by the above general formula (2) bonded to the carbon atoms at the fifth and sixth positions of the chromene ring; and ③  particular substituents are bonded to the carbon atom at the second position of the chromene ring.

As will become obvious from the comparison of Examples and Comparative Examples appearing later, possession of the above-mentioned three features in combination makes it possible to obtain excellent effects mentioned above.

It is desired that the chromene compound of the present invention is the one represented by the following general formula (6),

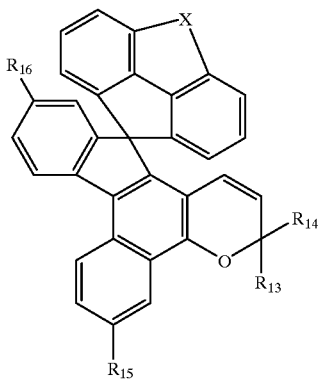

(6)

wherein $R^{15}$ and $R^{16}$ are, independently from each other, alkyl group with 1 to 4 carbon atoms, alkoxy group with 1 to 5 carbon atoms, aralkoxy group with 6 to 10 carbon atoms; mono-substituted or di-substituted amino group having, as a substituent, an aralkyl group with 1 to 4 carbon atoms or an aryl group with 6 to 10 carbon atoms, cyano group, aryl group with 6 to 10 carbon atoms, substituted aryl group with 6 to 10 carbon atoms (without including carbon atoms of a substituent) substituted with an alkyl group having 1 to 4 carbon atoms or an alkoxy group having 1 to 5 carbon atoms, halogen atom, or substituted or unsubstituted heterocyclic groups having a nitrogen atom as a hetero atom, being bonded to the indene ring or the naphthalene ring through the nitrogen atoms, and being selected from morpholino group, piperidino group, pyrrolidinyl group, 1-piperazinyl group, 4-methyl-1-piperazinyl group or indolinyl group, or condensed heterocyclic group in which said heterocyclic group is condensed with an aromatic hydrocarbon ring or an aromatic heterocyclic ring;

at least either one of $R^{13}$ and $R^{14}$ is a substituted aryl group with 6 to 10 carbon atoms (without including carbon atoms of a substituent) having at least one substituent selected from a mono-substituted or di-substituted amino group having, as a substituent, an alkyl group with 1 to 4 carbon atoms or an aryl group with 6 to 10 carbon atoms, alkoxy group with 1 to 5 carbon atoms, morpholino group, piperidino group, pyrrolidinyl group, 1-piperazinyl group, 4-methyl-1-piperazinyl group and indolinyl group, or a heteroaryl group with 4 to 12 carbon atoms (without including carbon atoms of a substituent); and X is a divalent group represented by —CH=CH—.

Among the above-mentioned chromene compounds, it is desired that the chromene compound is the one represented by the above formula (6) in which $R^{15}$ and $R^{16}$ are, independently from each other, alkyl group with 1 to 4 carbon atoms; alkoxy group with 1 to 5 carbon atoms, halogen atom, or morpholino group and, most desirably, methyl group or methoxyl group; at least either one of $R^{13}$ and $R^{14}$ is a substituted aryl group with 6 to 10 carbon atoms (without including carbon atoms of a substituent) having at least one substituent selected from a mono-substituted or di-substituted amino group having, as a substituent, an alkyl group with 1 to 4 carbon atoms or an aryl group with 6 to 10 carbon atoms, alkoxy group with 1 to 5 carbon atoms, morpholino group, piperidino group, pyrrolidinyl group, 1-piperazinyl group, 4-methyl-1-piperazinyl group and indolinyl group; and when either one of $R^{13}$ and $R^{14}$ is not the above group, the other one is an aryl group with 6 to 10 carbon atoms, or a heteroaryl group with 4 to 12 carbon atoms, and most desirably, either one of $R^{13}$ and $R^{14}$ is a phenyl group having a piperidino group, a morpholino group or a methoxyl group as a substituent, and the other one is a phenyl group or a methoxyphenyl group.

The invention is further concerned with a photochromic material comprising a chromene compound represented by the above-mentioned general formula (1), and with a photochromic optical material containing the chromene compound.

According to the present invention, there is further provided a photochromic polymerizable composition containing:

the above-mentioned chromene compound;
a polymerizable monomer (particularly, a (meth)acrylic acid ester compound); and
if necessary, a polymerization initiator.

DETAILED DESCRIPTION OF THE INVENTION

[Chromene Compound]

Figure 1:
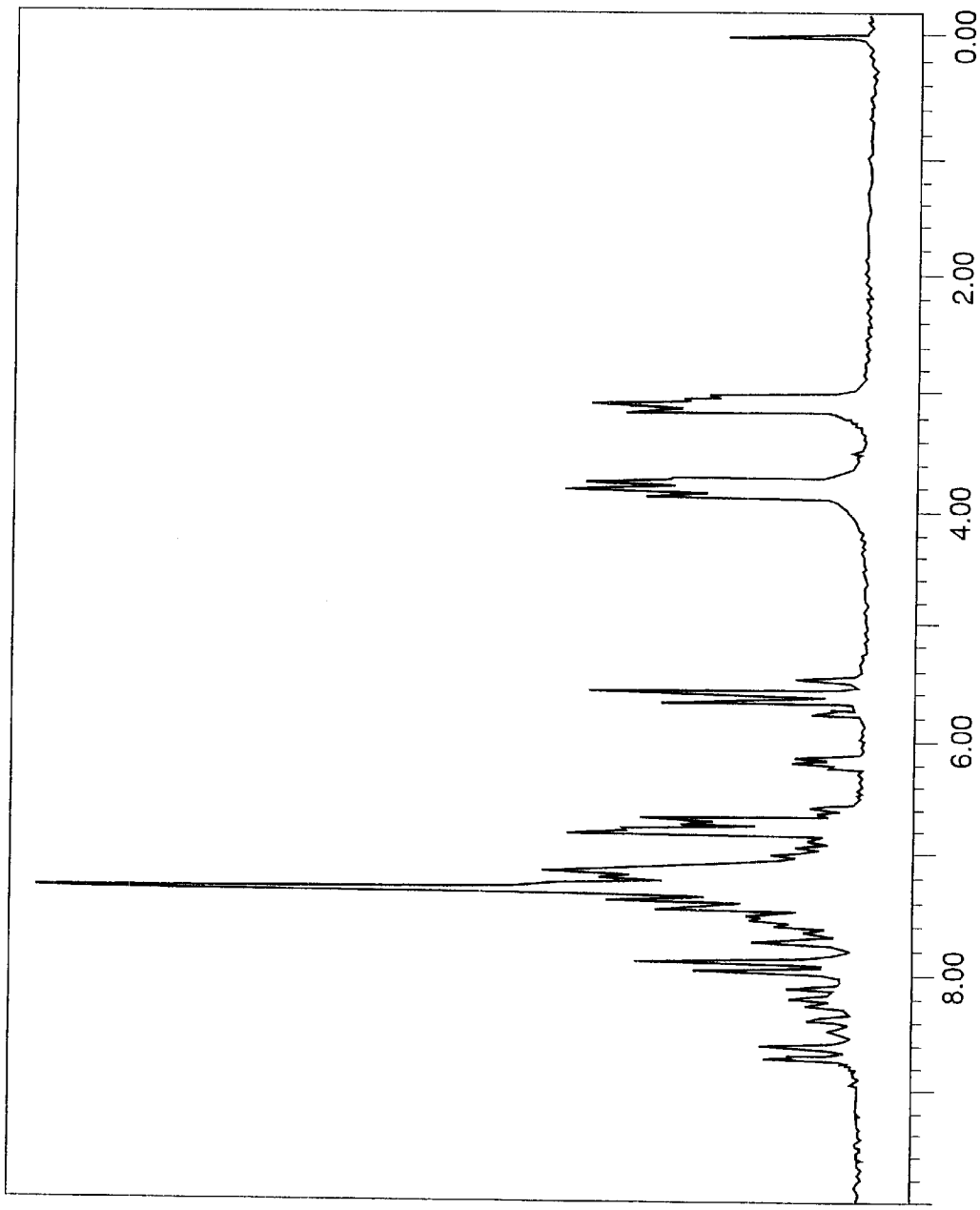
FIG. 1 is a diagram showing a proton nuclear magnetic resonance spectrum of a compound of Example 1.

In the above-mentioned general formula (1), $R^1$ is an alkyl group, a hydroxy group, an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the indene ring through the carbon atom, a monovalent substituted or unsubstituted heterocyclic group having a nitrogen atom as a hetero atom and bonded to the indene ring through the nitrogen atom, or a monovalent condensed heterocyclic group in which said heterocyclic group is condensed with an aromatic hydrocarbon ring or an aromatic heterocyclic ring.

The substituents represented by $R^1$ will now be described except the hydroxy group, amino group, cyano group, nitro group and trifluoromethyl group of which the structures have been known.

(a) Though there is no particular limitation, it is desired that the alkyl group generally has 1 to 4 carbon atoms. Preferred examples of the alkyl group include a methyl group, an ethyl group, an n-propyl group, an isopropyl group, an n-butyl group, a sec-butyl group, a t-butyl group, and the like groups.

(b) Though there is no particular limitation, it is desired that the alkoxy group generally has 1 to 5 carbon atoms. Preferred examples of the alkoxy group include a methoxyl group, an ethoxyl group, an n-propoxyl group, an isopropoxyl group, an n-butoxyl group, a sec-butoxyl group, a t-butoxyl group, and the like groups.

(c) Though there is no particular limitation, it is desired that the aralkoxy group generally has 6 to 10 carbon atoms. Preferred examples of the aralkoxy group include a phenoxy group, a naphthoxy group and the like groups.

(d) Though there is no particular limitation, it is desired that the substituted amino group is an alkylamino group, a dialkylamino group, an arylamino group or a diarylamino group, substituted by an alkyl group or an aryl group. Preferred examples of the substituted amino group include a methylamino group, an ethylamino group, a phenylamino group, a dimethylamino group, a diethylamino group, a diphenylamino group and the like groups.

(e) As for the substituted or unsubstituted aryl group, there is no particular limitation on the unsubstituted aryl group, but an unsubstituted aryl group with 6 to 10 carbon atoms is preferred. Preferred examples of the unsubstituted aryl group include a phenyl group, a naphthyl group and the like groups.

As the substituted aryl group, there can be exemplified those unsubstituted aryl groups in which one or two or more hydrogen atoms are substituted by a substituent. As the substituent, there can be exemplified an alkyl group, an alkoxy group, a substituted amino group, an aryl group, a substituted or unsubstituted heterocyclic group having a nitrogen atom as a hetero atom and bonded to the aryl group through the nitrogen atom, and a condensed heterocyclic ring in which said heterocyclic group is condensed with an aromatic hydrocarbon ring or the aromatic heterocyclic ring. Here, the alkyl group, alkoxy group and substituted amino group are the same as those denoted by $R^1$ above. Further, the substituted or unsubstituted heterocyclic group and condensed heterocyclic group are the same as the "substituted or unsubstituted heterocyclic group having a nitrogen atom as a hetero atom and is bonded to the indene ring through the nitrogen atom, and the condensed heterocyclic group in which the heterocyclic group is condensed with an aromatic hydrocarbon ring or an aromatic heterocyclic ring" denoted by $R^1$ except that the ring bonded through the nitrogen atom is changed from the indene ring to the aromatic ring of the aryl group. The details will be described later.

(f) As the halogen atom, there can be exemplified a fluorine atom, a chlorine atom, a bromine atom or an iodine atom.

(g) Though there is no particular limitation, it is desired that the aralkyl group has 7 to 11 carbon atoms. Preferred examples of the aralkyl group include a benzyl group, a phenylethyl group, a phenylpropyl group, a phenylbutyl group and the like groups.

(h) Though there is no particular limitation on the monovalent heterocyclic group bonded to the indene ring through the carbon atoms, preferred examples include a thienyl group, a furyl group or a pyrrolyl group.

(i) As the substituted or unsubstituted heterocyclic group having a nitrogen atom as a hetero atom and is bonded to the indene ring through the nitrogen atom, or as the condensed heterocyclic group in which the said heterocyclic group is condensed with the aromatic hydrocarbon atom or the aromatic heterocyclic ring, it is desired to use the one having carbon atoms in a number of 2 to 10 and, particularly, 2 to 6 to constitute the heterocyclic group, though there is no particular limitation. The heterocyclic ring may further include a hetero atom in addition to the nitrogen atom bonded to the indene ring. Though there is no particular limitation, the hetero atom is preferably an oxygen atom, a sulfur atom or a nitrogen atom. As the substituent for these groups, there can be exemplified the same groups as the substitutents for the substituted aryl group described in (e) above.

As the substituted or unsubstituted heterocyclic group having the nitrogen atom as a hetero atom and is bonded to the indene ring through the nitrogen atom, or as the condensed heterocyclic group in which the heterocyclic group is condensed with the aromatic hydrocarbon ring or the aromatic heterocyclic ring, there can be preferably exemplified a morpholino group, a piperidino group, a pyrrolidinyl group, a piperadino group, an N-methylpiperadino group and an indolinyl group.

Symbol p representing the number of substituents $R^1$ is an integer of from 0 to 3. There is limitation on neither the position at where $R^1$ is bonded nor the total number thereof but it is desired that the total number is not larger than 2. When p is 2 or 3, the substituents $R^1$ may be different from each other.

In the above-mentioned general formula (1), the divalent group represented by the following formula (2),

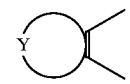

(2)

is a divalent aromatic hydrocarbon group or a divalent unsaturated heterocyclic group.

Though there is no particular limitation, it is desired that the divalent aromatic hydrocarbon group has 6 to 18 carbon atoms. Preferred examples of the divalent aromatic hydrocarbon group include unsubstituted aromatic hydrocarbon groups having a benzene ring such as phenylene group, naphthylene group, phenanthrylene group, tolylene group or xylylene group, or having 2 to 4 condensed rings thereof.

Though there is no particular limitation, it is desired the above-mentioned divalent unsaturated heterocyclic group is a 5-membered ring or a 6-membered ring having oxygen atom, sulfur atom or nitrogen atom, or a heterocyclic group in which the above ring is further condensed with a benzene ring. Preferred examples of the divalent unsubstituted and unsaturated heterocyclic group include nitrogen-containing heterocyclic groups such as pyridylene group, quinolylene group, pyrrolylene group, and indolylene group; oxygen-containing heterocyclic groups such as furylene group and benzofurylene group; and sulfur-containing heterocyclic groups such as thienylene group and benzothienylene group.

The aromatic hydrocarbon group or the unsaturated heterocyclic group may have a substituent $R^2$. Here, $R^2$ may be the same as $R^1$ and is an alkyl group, a hydroxy group, an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the ring of the group represented by the above formula (2) through a carbon atom, a monovalent substituted or unsubstituted heterocyclic group having a nitrogen atom as a hetero atom and is bonded to the ring of the group represented by the above formula (2) through the nitrogen atom, or a monovalent condensed heterocyclic group in which the heterocyclic group is condensed with the aromatic hydrocarbon atom or the aromatic heterocyclic ring.

Here, the "monovalent heterocyclic group bonded to the ring of the group represented by the above formula (2) through the carbon atom" and the "substituted or unsubstituted heterocyclic group having the nitrogen atom as a hetero atom and is bonded to the ring of the group represented by the above formula (2) through the nitrogen atom, or the condensed heterocyclic group in which the heterocyclic group is condensed with the aromatic hydrocarbon ring or the aromatic heterocyclic ring", are the same as the "monovalent heterocyclic group bonded to the indene ring through the carbon atom", the "substituted or unsubstituted heterocyclic group having the nitrogen atom as a hetero atom and is bonded to the indene ring through the nitrogen atom or the condensed heterocyclic group in which the heterocyclic group is condensed with the aromatic hydrocarbon ring or the aromatic heterocyclic ring" represented by $R^1$ except that the rings to which the nitrogen atom and the carbon atom are bonded are simply changed.

Symbol q representing the number of substituents $R^2$ is an integer of 0 to 3. There is limitation on neither the position at where $R^2$ is bonded nor the total number thereof but it is desired that the total number is not larger than 2. When q is 2 or 3, the substituents $R^2$ may be different from each other.

In the above-mentioned general formula (1), $R^3$ and $R^4$ are, independently from each other, group represented by the following formula (3),

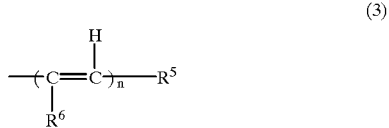

(3)

wherein $R^5$ is a substituted or unsubstituted aryl group, or substituted or unsubstituted heteroaryl group, $R^6$ is a hydrogen atom, an alkyl group or a halogen atom, and n is an integer of 1 to 3;

group represented by the following formula (4),

(4)

wherein $R^7$ is a substituted or unsubstituted aryl group, or substituted or unsubstituted heteroaryl group, and m is an integer of 1 to 3;

substituted or unsubstituted aryl group; or substituted or unsubstituted heteroaryl group.

In the general formula (1), further, $R^3$ and $R^4$ are not limited to these groups only, but $R^3$ and $R^4$ together may constitute an aliphatic hydrocarbon ring or an aromatic hydrocarbon ring.

In the above-mentioned general formula (3), $R^5$ is a substituted or unsubstituted aryl group, or a substituted or unsubstituted heteroaryl group. As the substituted or unsubstituted aryl group, there can be used the group same as the substituted or unsubstituted aryl group denoted by $R^1$ or $R^2$.

In the substituted aryl group, there is no particular limitation on the position at where the substituent is bonded, and there is no particular limitation on the total number of the substituents, either. It is, however, desired that the aryl group is bonded at the third position or the fourth position when it is a phenyl group, and is bonded at the fourth position or the sixth position when it is a naphthyl group.

Though there is no particular limitation, it is desired that the unsubstituted heteroaryl group has 4 to 12 carbon atoms. Concrete examples include a thienyl group, a furyl group, a pyrrolinyl group, a pyridyl group, a benzothienyl group, a benzofuranyl group and a benzopyrrolinyl group. As the substituted heteroaryl group, there can be exemplified the above unsubstituted heteroaryl group of which one or two or more hydrogen atoms are substituted by the same groups as the substituents of the substituted aryl group of $R^1$ or $R^2$. There is no particular limitation on the positions at where these substituents are bonded, and there is no particular limitation on the total number thereof either.

In the above-mentioned formula (3), $R^6$ is a hydrogen atom, an alkyl group or a halogen atom. Preferred examples of the alkyl group include a methyl group, an ethyl group and a propyl group. Further, concrete examples of the halogen atom include a fluorine atom, a chlorine atom, a bromine atom and an iodine atom.

In the general formula (3), n is an integer of 1 to 3. It is desired that n is 1 from the standpoint of easily obtaining the starting material.

Preferred examples of the group represented by the above-mentioned general formula (3) include phenylethenyl group, (4-(N,N-dimethylamino)phenyl)ethenyl group, (4-(N,N-diethylamino)phenyl)ethenyl group, (4-morpholinophenyl)ethenyl group, (4-piperidinophenyl) ethenyl group, (4-julolidinophenyl)ethenyl group, (4-methoxyphenyl)ethenyl group, (4-methylphenyl)ethenyl group, (2-(N,N-dimethylamino)phenyl)ethenyl group, (2-methoxyphenyl)ethenyl group, phenyl-1-methylethenyl group, (4-(N,N-dimethylamino)phenyl)-1-methylethenyl group, (4-methoxyphenyl)-1-methylethenyl group, phenyl-1-fluoroethenyl group, (4-(N,N-dimethylamino)phenyl)-1-fluoroethenyl group, 2-thienylethenyl group, 2-furylethenyl group, 2-(N-methyl)pyrrolinylethenyl group, 2-benzothienyethenyl group, 2-benzofuranylethenyl group and 2(N-methyl)indolylethenyl group.

In the above-mentioned formula (4), $R^7$ is a substituted or unsubstituted aryl group, or a substituted or unsubstituted heteroaryl group. These groups are the same as the groups denoted by $R^5$ above.

In the above-mentioned formula (4), there is no particular limitation on m provided it is an integer of 1 to 3. Desirably, however, m is 1 from the standpoint of easily obtaining the starting material.

Preferred examples of the group represented by the above-mentioned general formula (4) include phenylethynyl group, (4-(N,N-dimethylamino)phenyl)ethynyl group, (4-(N,N-diethylamino)phenyl)ethynyl group, (4-morpholinophenyl)ethynyl group, (4-piperidinophenyl) ethynyl group, (4-julolidinophenyl)ethynyl group, (4-methoxyphenyl)ethynyl group, (4-methylphenyl)ethynyl group, (2-(N,N-dimethylamino)phenyl)ethynyl group, (2-methoxyphenyl)ethynyl group, 2-thienylethynyl group, 2-furylethynyl group, 2-(N-methyl)pyrrolinylethynyl group, 2-benzothienyethynyl group, 2-benzofuranylethynyl group and 2(N-methyl)indolylethynyl group.

The substituted or unsubstituted aryl group, or substituted or unsubstituted heteroaryl group of $R^3$ or $R^4$ are the same as the groups denoted by $R^6$.

There is no particular limitation on the aliphatic hydrocarbon ring formed by $R^3$ and $R^4$ together. Its preferred examples include an adamantilydene ring, a bicyclononylidene ring and norbornylidene ring.

Further, there is no particular limitation on the aromatic hydrocarbon ring formed by $R^3$ and $R^4$ together. Its preferred examples include a fluorene ring and the like.

It is desired that at least one of $R^3$ or $R^4$ is a substituted or unsubstituted aryl group, or a substituted or unsubstituted heteroaryl group, or a group having these groups.

It is further particularly desired that at least one of $R^3$ or $R^4$ is any one of the groups represented by (i) to (ix) below in addition to the aryl group having an alkoxy with 1 to 5 carbon atoms as a substituent:

(i) a substituted aryl group or a substituted heteroaryl group having a substituted amino group as a substituent;

(ii) a substituted aryl group or a substituted heteroaryl group having a substituted or unsubstituted heterocyclic group as a substituent, the heterocyclic group having a nitrogen atom as a hetero atom and in which the nitrogen atom is bonded to the aryl group or to the heteroaryl group;

(iii) a substituted aryl group or a substituted heteroaryl group having, as a substituent, a condensed heterocyclic group in which the substituted or unsubstituted heterocyclic group of (ii) above is condensed with an aromatic hydrocarbon ring or an aromatic heterocyclic ring;

(iv) a group represented by the formula (3) in which $R^5$ is a substituted aryl group or a substituted heteroaryl group having a substituted amino group as a substituent;

(v) a group represented by the formula (3) in which $R^5$ is a substituted aryl group or a substituted heteroaryl group having, as a substituent, a substituted or unsubstituted heterocyclic group having a nitrogen atom as a hetero atom, and the nitrogen atom being bonded to the aryl group or to the heteroaryl group;

(vi) a group represented by the formula (3) in which $R^5$ is a substituted aryl group or a substituted heteroaryl group having, as a substituent, a condensed heterocyclic group in which the substituted or unsubstituted heterocyclic group in (v) above is condensed with an aromatic hydrocarbon ring or an aromatic heterocyclic ring;

(vii) a group represented by the formula (4) in which $R^7$ is a substituted aryl group or a substituted heteroaryl group having a substituted amino group as a substituent;

(viii) a group represented by the formula (4) in which $R^7$ is a substituted aryl group or a substituted heteroaryl group having, as a substituent, a substituted or unsubstituted heterocyclic group with the nitrogen atom being bonded to the aryl group or to the heteroaryl group; or (ix) a group represented by the formula (4) in which $R^7$ is a substituted aryl group or a substituted heteroaryl group having, as a substituent, a condensed heterocyclic group in which the substituted or unsubstituted heterocyclic group in (viii) above is condensed with an aromatic hydrocarbon ring or an aromatic heterocyclic ring.

In the substituted aryl groups in (i) to (iii) above, there is no particular limitation on the position at where the substituent is substituted and there is, either, no particular limitation on the total number thereof. It is, however, desired that the substituent is substituted at the third position or at the fourth position when the aryl group is a phenyl group and its number is 1. Preferred examples of the substituted aryl group include 4-(N,N-dimethylamino)phenyl group, 4-(N,N-diethylamino)phenyl group, 4-(N,N-diphenylamino)phenyl group, 4-morpholinophenyl group, 4-piperidinophenyl group and 3-(N,N-dimethylamino)phenyl group.

In the substituted heteroaryl groups in (i) to (iii) above, there is no particular limitation on the position at where the substituent is substituted and there is, either, no limitation on the total number thereof. It is, however, desired that the total number is 1. Preferred examples of the substituted heteroaryl group include 4-(N,N-dimethylamino)thienyl group, 4-(N,N-diethylamino)furyl group, 4-(N,N-diphenylamino)thienyl group, 4-morpholinopyrrolinyl group, 6-piperidinobenzothienyl group, and 6-(N,N-dimethylamino)benzofuranyl group.

In the groups represented by the formula (3) of (iv) to (vi) described above, $R^5$ stands for the substituted aryl group or the substituted heteroaryl group of (i) to (iii) above. Preferred examples of the group represented by the formula (3) include (4-(N,N-dimethylamino)phenyl)ethenyl group, (4-(N,N-diethylamino)phenyl)ethenyl group, (4-morpholinophenyl)ethenyl group, (4-piperidinophenyl)ethenyl group, (4-julidinophenyl)ethenyl group, (2-(N,N-dimethylamino)phenyl)ethenyl group, (4-(N,N-dimethylamino)phenyl)-1-methylethenyl group, and (4-(N,N-dimethylamino)phenyl)-1-fluoroethenyl group.

In the groups represented by the formula (4) of (vii) to (ix) described above, $R^7$ stands for the same substituted aryl group or the substituted heteroaryl group of (i) to (iii) above. Preferred examples of the group represented by the formula (4) include (4-(N,N-dimethylamino)phenyl)ethynyl group, (4-(N,N-diethylamino)phenyl)ethynyl group, (4-morpholinophenyl)ethynyl group, (4-piperidinophenyl)ethynyl group, (4-julidinophenyl)ethynyl group, (2-(N,N-dimethylamino)phenyl)ethynyl group, 2-(N-methyl)indolylethynyl group, and (4-(N-methylpiperadino)phenyl)ethynyl group.

In the above-mentioned general formula (1), X is a group represented by any one of

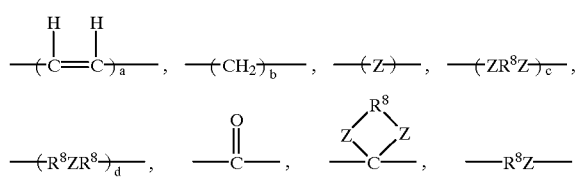

wherein Z is an oxygen atom or a sulfur atom, and $R^8$ is an alkylene group.

Though there is no particular limitation, it is desired that the alkylene group has 1 to 6 carbon atoms. Preferred examples of the alkylene group include methylene group, ethylene group, propylene group, butylene group, pentylene group and hexylene group. In the formulas, symbols a, b, c and d represent the recurring numbers and are all integers of 1 to 4. Among them, it is desired that they are all 1 or 2 from the standpoint of easy production.

In the present invention, the chromene compound of the following formula (5) is preferred from the standpoint of fading rate, (5)

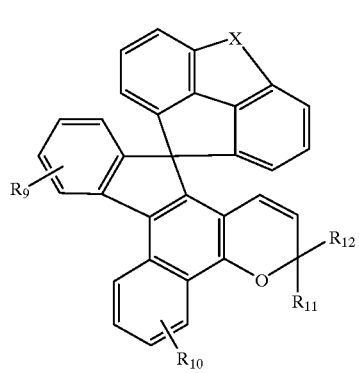

wherein $R^9$ and $R^{10}$ are, independently from each other, hydrogen atom, alkyl group, alkoxy group, aralkoxy group, substituted amino group, cyano group, substituted or unsubstituted aryl group, halogen atom, aralkyl group, substituted or unsubstituted heterocyclic group having a nitrogen atom as a hetero atom and are bonded to the indene ring (in the case of $R^9$) or to a naphthalene ring (in the case of $R^{10}$) through the nitrogen atom, or condensed heterocyclic group in which the heterocyclic group is condensed with an aromatic hydrocarbon ring or an aromatic heterocyclic ring, $R^{11}$ and $R^{12}$ are, independently from each other, substituted or unsubstituted aryl groups, or substituted or unsubstituted heteroaryl group, and X is a group represented by any one of,

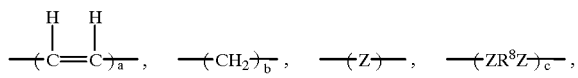

wherein Z is an oxygen atom or a sulfur atom, $R^8$ is an alkylene group with 1 to 6 carbon atoms, and symbols a, b, c and d are integers of 1 to 4.

From the standpoint of fading rate and color-developing sensitivity, further, it is particularly desired that the chromene compound is the one represented by the above-mentioned general formula (5) but in which $R^9$ and $R^{10}$ are particular substituents which are not hydrogen atoms with their positions of substitution being specified, and $R^{11}$, $R^{12}$ and X are further specified, i.e., the chromene compound is the one represented by the following general formula (6), (6)

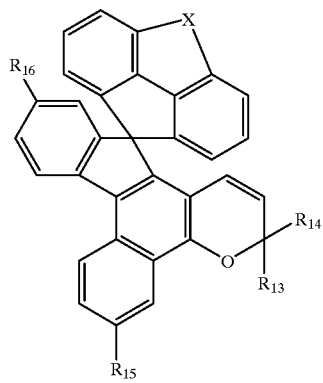

wherein $R^{15}$ and $R^{16}$ are, independently from each other, alkyl group with 1 to 4 carbon atoms, alkoxy group with 1 to 5 carbon atoms, aralkoxy group with 6 to 10 carbon atoms; mono-substituted or di-substituted amino group having, as a substituent, an aralkyl group with 1 to 4 carbon atoms or an aryl group with 6 to 10 carbon atoms, cyano group, aryl group with 6 to 10 carbon atoms, substituted aryl group with 6 to 10 carbon atoms (without including carbon atoms of a substituent) substituted with an alkyl group having 1 to 4 carbon atoms or an alkoxy group having 1 to 5 carbon atoms, halogen atom, or substituted or unsubstituted heterocyclic groups having a nitrogen atom as a hetero atom, being bonded to the indene ring or the naphthalene ring through the nitrogen atoms, and being selected from morpholino group, piperidino group, pyrrolidinyl group, 1-piperazinyl group, 4-methyl-1-piperazinyl group or indolinyl group, or condensed heterocyclic group in which said heterocyclic group is condensed with an aromatic hydrocarbon ring or an aromatic heterocyclic ring;

at least either one of $R^{13}$ and $R^{14}$ is a substituted aryl group with 6 to 10 carbon atoms (without including carbon atoms of a substituent) having at least one substituent selected from a mono-substituted or di-substituted amino group having, as a substituent, an alkyl group with 1 to 4 carbon atoms or an aryl group with 6 to 10 carbon atoms, alkoxy group with 1 to 5 carbon atoms, morpholino group, piperidino group, pyrrolidinyl group, 1-piperazinyl group, 4-methyl-1-piperazinyl group and indolinyl group, or a heteroaryl group with 4 to 12 carbon atoms (without including carbon atoms of a substituent); and X is a divalent group represented by —CH=CH—.

Among the chromene compounds represented by the above general formula (6), it is most desired, from the standpoint of effects, that the chromene compound is the one represented by the above general formula (6) but in which $R^{15}$ and $R^{16}$ are, independently from each other, alkyl group with 1 to 4 carbon atoms, alkoxy group with 1 to 5 carbon atoms, halogen atom or morpholino group; at least either one of $R^{13}$ and $R^{14}$ is a substituted aryl group with 6 to 10 carbon atoms (without including carbon atoms of a substituent) having at least one substituent selected from a mono-substituted or di-substituted amino group having, as a substituent, an alkyl group with 1 to 4 carbon atoms or an aryl group with 6 to 10 carbon atoms, alkoxy group with 1 to 5 carbon atoms, morpholino group, piperidino group, pyrrolidinyl group, 1-piperazinyl group, 4-methyl-1-piperazinyl group or indonlinyl group; and either one of $R^{13}$ and $R^{14}$, when they do not stand for those groups described above, is an aryl group with 6 to 10 carbon atoms.

As will be described later in Examples, the above most desired chromene compound exhibits less initial color, a high color density, a high durability of photochromic property and, besides, requires a very short period of time until the developing of color is completed from the start of irradiation with light from the source of light (concretely, color-developing sensitivity of not longer than 45 seconds as referred to in Examples) and a short period of time until color fades from when irradiation with light is discontinued (concretely, fading rate of not longer than 2 minutes as referred to in Examples), which are excellent photochromic properties. Concrete examples of the most preferred chromene compounds are as follows:

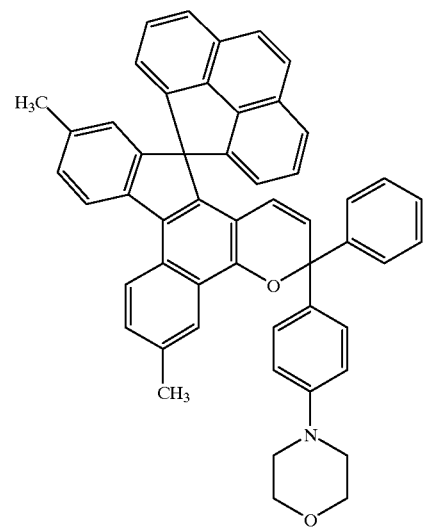

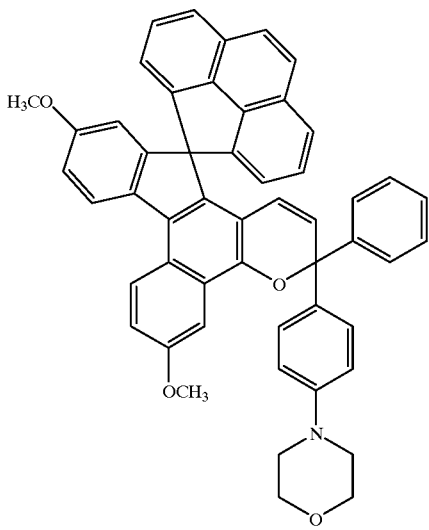

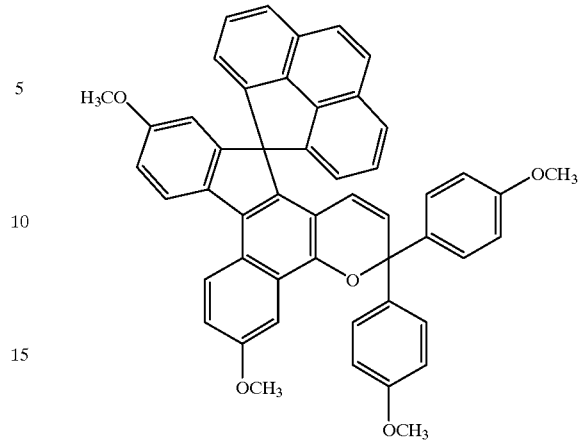

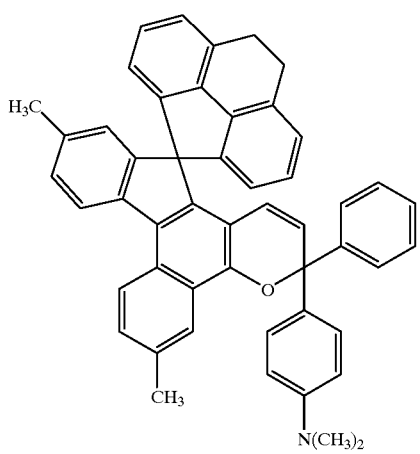

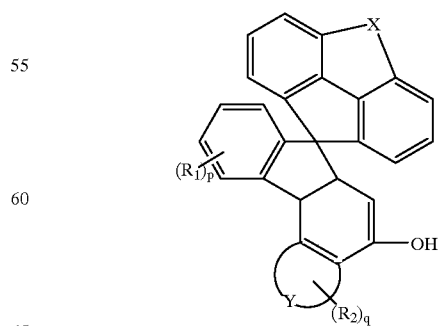

The chromene compound of the present invention represented by the above-mentioned general formula (1) usually exists in the form of a colorless or pale yellow solid or a viscous liquid under the conditions of a normal temperature and a normal pressure, and can be confirmed by the following means (a) to (c).

(a) The proton nuclear magnetic resonance spectrum ($^1$H-NMR) shows peaks due to aromatic protons and protons of alkenes near δ5.0 to 9.0 ppm, and peaks due to protons of an alkyl group and an alkylene group near δ1.0 to 4.0 ppm. Further, comparison of the spectral intensities indicates the number of protons present in the respective bonding groups.

(b) Elemental analysis makes it possible to determine the compositions of the corresponding products.

(c) The $^{13}$C-nuclear magnetic resonance spectrum ($^{13}$C-NMR) shows peaks due to carbon of an aromatic hydrocarbon group near δ110 to 160 ppm, peaks due to carbon of alkenes and alkynes near δ80 to 140 ppm, and peaks due to carbon of an alkyl group and an alkylene group near δ20 to 80 ppm.

[Preparation of Chromene Compounds]

The chromene compounds of the present invention represented by the general formula (1) may be prepared by any method without being particularly limited. Described below are a process A and a process B which are representative methods preferably employed.

Process A

In this process, a hydroxyfluorene derivative represented by the following general formula (7), (7)

wherein $R^1$, $R^2$, X, p, q and a divalent group represented by the following formula

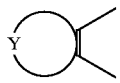

(2)

are as defined in the above-mentioned general formula (1), and a propargyl alcohol derivative represented by the general formula (8),

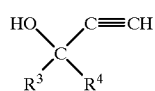

(8)

wherein $R^3$ and $R^4$ are as defined in the above-mentioned general formula (1),
are reacted with each other in the presence of an acid catalyst.

There is no particular limitation on the methods of synthesizing the hydroxyfluorene derivative represented by the above general formula (7) and the propargyl alcohol derivative represented by the general formula (8). The hydroxyfluorene derivative represented by the above general formula (7) is synthesized by, for example, reacting a hydroxyfluorenone derivative with the Grignard reagent at −10 to 70° C. for 10 minutes to 4 hours to obtain a hydroxyfluorenole derivative followed by the reaction under an acidic condition at 10 to 120° C. for 10 minutes to 2 hours to convert the fluorenole into the spiro form. When there is used a hydroxyfluorenone derivative having a substituent on the Y-ring of the hydroxyfluorenone derivative, there can be synthesized a chromene compound having substituents on the respective Y-rings. Further, the propargyl alcohol derivative represented by the above general formula (8) is synthesized by, for example, reacting a ketone derivative corresponding to the above general formula (8) with a metal acetylene compound such as lithium acetylide.

The reaction of the compound represented by the above general formula (7) with the compound represented by the general formula (8) in the presence of an acid catalyst, is conducted, for example, in a manner as described below.

The ratio of reaction of these two kinds of compounds can be selected over a wide range. Generally, however, the ratio of the former compound to the latter compound is selected over a range of from 1:10 to 10:1 (molar ratio). As the acid catalyst, there is used sulfuric acid, benzenesulfonic acid, p-toluenesulfonic acid or acidic alumina in an amount of from 0.1 to 10 parts by weight per 100 parts by weight of the compound represented by the above general formula (7) and the compound (reaction substrate) represented by the formula (8). Preferably, the reaction temperature is generally from 0 to 200° C., and the solvent that is used is a nonprotonic organic solvent such as N-methylpyrrolidone, dimethylformamide, tetrahydrofuran, benzene or toluene.

Process B

In this process, a hydroxyfluorenone derivative represented by the following general formula (9),

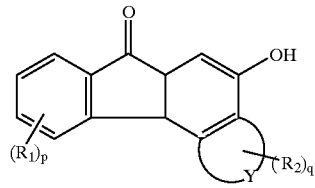

(9)

wherein $R^1$, $R^2$, p, q and a divalent group represented by following formula

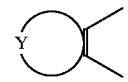

(2)

are as defined in the above-mentioned general formula (1), and a propargyl alcohol derivative represented by the general formula (8),

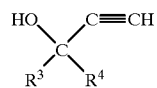

(8)

wherein $R^3$ and $R^4$ are as defined in the above-mentioned general formula (1),
reacted with each other in the presence of an acid catalyst to once obtain a chromene compound (hereinafter abbreviated as precursor chromene compound 1) of the following general formula (10),

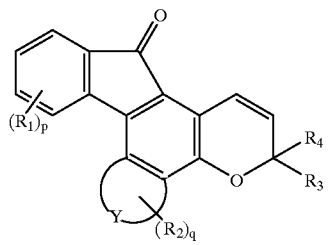

(10)

wherein $R^1$, $R^2$, $R^3$, $R^4$, p, q and a divalent group represented by following formula

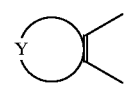

(2)

are as defined in the above-mentioned general formula (1), and, then, the precursor chromene compound 1 is reacted with the Grignard reagent at −10 to 70° C. for 10 minutes to 4 hours in the same manner as the method of synthesizing the compound of the above general formula (7), thereby to obtain a fluorenol-chromene derivative (hereinafter abbreviated as precursor chromene compound 2) followed by the reaction under acidic condition at 10 to 120° C. for 10 minutes to 2 hours to convert the fluorenol moiety of the precursor chromene compound 2 into the spiro form, thereby to obtain the chromene compound of the above-mentioned general formula (1).

When there is used a hydroxyfluorenone derivative having a substituent on the Y-ring of the hydroxyfluorenone derivative, there can be synthesized a chromene compound having substituents on the respective Y-rings.

The reaction of the compound represented by the above general formula (9) with the compound represented by the general formula (8) in the presence of an acid catalyst, is conducted, for example, in a manner as described below.

The ratio of reaction of these two kinds of compounds can be selected over a wide range. Generally, however, the ratio of the former compound to the latter compound is selected over a range of from 1:10 to 10:1 (molar ratio). As the acid catalyst, there is used sulfuric acid, benzenesulfonic acid, p-toluenesulfonic acid or acidic alumina in an amount of from 0.1 to 10 parts by weight per 100 parts by weight of the total reaction substrates represented by the above general formulas (9) and (8). Preferably, the reaction temperature is generally from 0 to 200° C., and the solvent that is used is a nonprotonic organic solvent such as N-methylpyrrolidone, dimethylformamide, tetrahydrofuran, benzene or toluene.

The reaction for converting the precursor chromene compound 1 into the compound represented by the above-mentioned general formula (1) is conducted in a manner as described below.

That is, the precursor chromene compound 1 is reacted with the Grignard reagent to obtain the precursor chromene compound 2. The ratio of reaction of these two kinds of compounds is selected over a wide range. Generally, however, the ratio of the former compound to the latter compound is selected over a range of from 1:10 to 10:1 (molar ratio). The reaction temperature is, generally, from −10 to 70° C. and the solvent is a nonprotonic organic solvent, such as diethyl ether, tetrahydrofurane, benzene or toluene.

Thereafter, the seventh position of the (7H)benzo(c) fluorene-7-ol-chromene derivative which is the precursor chromene compound 2 that is obtained, is converted into the spiro form under acidic condition. Here, as the acid catalyst, there is preferably used acetic acid, hydrochloric acid, sulfuric acid, benzenesulfonic acid, p-toluenesulfonic acid or acidic alumina in an amount of from 0.1 to 10 parts by weight per 100 parts by weight of the precursor chromene compound 2. Preferably, the reaction temperature is generally from 0 to 120° C. and the solvent that is used is, for example, acetic acid, tetrahydrofuran, benzene or toluene.

Though there is no particular limitation, the product is refined by, for example, the silica-gel column refining method, which may further be followed by recrystallization to further refine the product.

[Photochromic Material]

The chromene compound of the present invention represented by the above-mentioned general formula (1) dissolves in a general organic solvent such as toluene, chloroform or tetrahydrofuran. The above solvent in which the chromene compound represented by the general formula (1) is dissolved, is generally almost colorless and transparent, and exhibits a favorable photochromic action in that it quickly develops a color when irradiated with sun light or ultraviolet rays, and reversibly and quickly returns to its initial colorless state when it is no longer irradiated with light.

The compound of the general formula (1) also exhibits the same photochromic action even in a high-molecular solid matrix. Any high-molecular solid matrix can be used provided the chromene compound represented by the general formula (1) of the present invention homogeneously disperses therein. Optically preferred examples include thermoplastic resins such as poly(methylacrylate), poly (ethylacrylate), poly(methylmethacrylate), ethyl poly (ethylmethacrylate), polystyrene, polyarylonitrile, polyvinyl alcohol, polyacrylamide, poly(2-hydroxyethyl methacrylate), poly(dimethyl siloxane) and polycarbonate.

There can be further exemplified thermosetting resins obtained by polymerizing radically polymerizable polyfunctional monomers including (meth)acrylic ester compounds having two or more (meth)acryloyloxy group such as ethylene glycol diacrylate, diethylene glycol dimethacrylate, triethylene glycol dimethacrylate, tetraethylene glycol dimethacrylate, nonaethylene glycol dimethacrylate, tetradecaethylene glycol dimethacrylate, ethylene glycol bisglycidyl methacrylate, bisphenol A dimethacrylate, 2,2-bis(4-methacryloyloxyethoxyphenyl)propane, 2,2-bis(3,5-dibromo-4-methacryloyloxyethoxyphenyl)propane, trimethylolpropane trimethacrylate and pentaerithritol trimethacrylate; polyallyl compounds such as diallyl phthalate, diallyl terephthalate, diallyl isophthalate, diallyl tartarate, diallyl epoxysuccinate, diallyl fumarate, diallyl ohlorendate, diallyl hexaphthalate, diallyl carbonate, diallyl diglycol carbonate, and trimethylolpropane triallyl carbonate; poly thioacrylic acid or poly thiomethacrylic acid ester compounds, such as 1,2-bis(methacryloylthio)ethane, bis(2-acryloylthioethyl)ether, and 1,4-bis (methacryloylthiomethyl)benzene; (meth)acrylic ester compounds having one or more functional group except for (meth)acryloyloxy group, such as glycidyl acrylate, glycidyl methacrylate, β-methylglycidyl methacrylate, bisphenol A-monoglycidyl ether methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate, polyethylene glycol methacrylate, polypropylene glycol methacrylate, and polytetramethylene glycol methacrylate; and divinyl benzene, etc.

There can be further exemplified copolymers obtained by polymerizing the above monomers with radically polymerizable monofunctional monomers including unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate and 2-hydroxyethyl methacrylate; fumaric acid ester compounds such as diethyl fumarate and diphenyl fumarate; thioacrylic acid and thiomethacrylic acid ester compounds such as methylthio acrylate, benzylthio acrylate and benzylthio methacrylate; and vinyl compounds such as styrene, chlorostyrene, methyl styrene, vinyl naphthalene, α-methylstyrene dimer and bromostyrene.

The chromene compound of the present invention represented by the general formula (1) is dispersed in the above-mentioned high-molecular solid matrix by a generally employed method without any particular limitation. For example, the thermoplastic resin and the chromene compound are kneaded together in a molten state, and are dispersed in the resin. Or, the chromene compound is dissolved in the polymerizable monomer, and is polymerized by adding a polymerization catalyst thereto and applying heat or light to disperse it in the resin. Or, the surfaces of the thermoplastic resin and of the thermosetting resin are dyed with the chromene compound so that it is dispersed in the resin.

The chromene compound of the present invention can be extensively utilized as a photochromic material, such as various memory materials to substitute for a silver salt photosensitive material, and as various memory materials like copying material, photosensitive material for printing, memory material for Cathode Ray Tube (CRT), photosensitive material for laser beams, and photosensitive material for holography. The photochromic material using the chromene compound of the present invention can be utilized as optical materials like photochromic lens material, optical filter material, display material, actinometer and ornament.

When used for the photochromic lens, for example, there is imposed no particular limitation provided a uniformly dimming performance is obtained. Concrete examples include a method in which a polymer film having the photochromic material of the invention homogeneously dispersed therein is sandwiched in a lens, a method in which the chromene compound of the invention is dispersed in the above-mentioned polymerizable monomer and is polymerized according to a predetermined method, or a method in which the compound is dissolved in, for example, a silicone oil so that the lens surfaces are impregnated therewith at 150 to 200° C. for 10 to 60 minutes, and the surfaces are coated with a curable substance to obtain a photochromic lens. Further, the polymer film may be applied to the surfaces of the lens, and the surfaces may be coated with a curable substance to obtain a photochromic lens.

[Photochromic Polymerizable Composition]

Among the above-mentioned photochromic materials, the photochromic polymerizable composition obtained by dispersing the chromene compound of the invention in a polymerizable monomer is used particularly when it is intended to prepare a photochromic material of a high-molecular matrix.

For example, the photochromic polymerizable composition mentioned above is poured into a desired metal mold and is polymerized by using a catalyst for polymerization to obtain a product.

The photochromic polymerizable composition contains a chromene compound of the present invention, a polymerizable monomer and, if necessary, a polymerization initiator.

<Polymerizable Monomer>

As the polymerizable monomer, there can be exemplified the one that is capable of forming the above-mentioned high-molecular matrix. Among them, the (meth)acrylic ester compound is most desired from the standpoint of transparency of the obtained polymer, dimensional stability and machinability.

<Polymerization Initiator>

A radical polymerization initiator is usually used as a polymerization initiator. Representative examples include diallyl peroxides such as benzoyl peroxide, p-chlorobenzoyl peroxide, decanoyl peroxide, lauroyl peroxide, and acetyl peroxide; peroxy esters such as t-butylperoxy-2-ethyl hexanate, t-butylperoxy neodecanate, cumylperoxy neodecanate, t-butylperoxy benzoate, t-butylperoxy isobutylate, and 1,1,3,3-tetramethylbutylperoxy-2-ethyl hexanate; percarbonates such as diisopropylperoxy carbonate and di-sec-butylperoxy dicarbonate; and azo compounds such as azobisisobutylonitrile. As the catalyst for photo polymerization, there can be exemplified acetophenone compounds such as 1-phenyl-2-hydroxy-2-methylpropane-1-one, 1-hydroxycyclohexylphenyl ketone, 1-(4-isopropylphenyl)-2-hydroxy-2-methylpropane-1-one; α-carbonyl compounds such as 1,2-diphenylethane dione, and methylphenyl glyoxylate; and acylphosphine oxide compounds such as 2,6-dimethylbenzoyldiphenylphosphine oxide, 2,4,6-trimethylbenzoyldiphenylphosphine oxide, 2,6-dichlorobenzoyldiphenylphosphine oxide, 2,6-dimethoxybenzoyldiphenylphosphine oxide. These polymerization initiators may be used in one kind or may be used in two or more kinds at any ratio depending upon the monomer that is used. Further, there may be used a thermal polymerization catalyst and a photo polymerization catalyst in combination. When the photo polymerization catalyst is used, there may be used a known polymerization promotor such as tertiary amine or the like.

The amount of the polymerization initiator that is used varies depending upon the polymerization conditions, kind of the initiator, composition of the polymerizable monomer, and cannot be definitely limited. In general, however, the polymerization initiator is used in an amount of from 0.001 to 10 parts by weight and, preferably, from 0.01 to 5 parts by weight per 100 parts by weight of the whole polymerizable monomer.

<Other Components>

In order to improve properties, furthermore, the photochromic polymerizable composition of the present invention may be blended with various additives depending upon the use of the photochromic material that is obtained by polymerizing and curing the polymerizable composition, within a range in which it does not impair the curing of the invention.

The chromene compound used in the invention develops a color tone of, for example, yellow to purple color. However, it may be combined with other known photochromic compound to obtain a photochromic composition that develops a neutral tint such as grey, amber or brown, which is generally preferred as a photochromic lens. There is no particular limitation on the other photochromic compound that is used in combination, and any known photochromic compound can be used, such as oxazine compound, fulgimide compound and/or a known chromene compound (hereinafter referred to as "other known chromene compound") other than the chromene compound used in the invention.

In the invention, there is no particular limitation on the mixing ratio of these oxazine compound, fulgimide compound and other known chromene compounds, and the mixing ratio may be suitably determined by taking the properties of the photochromic compounds into consideration. When the oxazine compound, fulgimide compound and/or other known chromene compounds are to be added to the photochromic polymerizable composition of the invention, these compounds are added in an amount of, usually, from 0.001 to 10 parts by weight and, preferably, from 0.01 to 1 part by weight per 100 parts by weight of the whole monomer.

Further, an ultraviolet ray stabilizer may be added to the photochromic polymerizable composition of the present invention. Addition of the ultraviolet ray stabilizer further improves the photochromic light resistance. When the fulgimide compound is used in particular, improvement in the light resistance is recognized. Therefore, when the above-mentioned oxazine compound and fulgimide compound are used in combination to develop a neutral tint, the color tone of the neutral tint that is developed does not change with the passage of time.

Any known ultraviolet ray stabilizer can be used without limitation and, preferably, there can be used a hindered amine photo stabilizer, a hindered phenol photo stabilizer, a sulfur-type antioxidant, or a phosphorous acid ester-type photo stabilizer.

Though there is no particular limitation, the above-mentioned ultraviolet ray stabilizer is usually used in an amount of from 0.01 to 5 parts by weight and, preferably, from 0.02 to 1 part by weight per 100 parts by weight of the whole monomer.

If necessary, further, there may be added various additives such as benzotriazole-type ultraviolet ray absorber, benzophenone-type ultraviolet ray absorber, antioxidant, coloring-preventing agent, antistatic agent, fluorescent dyes, pigments and perfumes.

<Polymerization and Curing of Polymerizable Composition>

Described below is how to obtain the photochromic material of the present invention by polymerizing and curing the photochromic polymerizable composition of the present invention.

There is no particular limitation on the polymerization method of obtaining a polymer from the photochromic polymerizable composition of the present invention, and any known polymerization method can be employed. The polymerization is carried out by using various peroxides, a polymerization initiator such as azo compound, or by the irradiation with ultraviolet rays, α-rays, β-rays, γ-rays, or by using both of them. A representative polymerization method is a cast polymerization in which the photochromic polymerizable composition of the invention containing a radical polymerization initiator is poured into a mold that is held by elastomer gaskets or spacers, and is polymerized in a heating furnace or by being irradiated with ultraviolet rays or visible rays and is, then, taken out.

Among the polymerization conditions, the polymerization temperature varies depending upon the kind of the polymerizable monomer or the kind of the polymerization initiator and cannot be definitely determined. In general, however, a so-called taper-type two-stage polymerization is conducted, in which the polymerization starts at a relatively low temperature, the temperature is gradually elevated, and the curing is effected at the end of the polymerization at a high temperature. Like the temperature, the polymerization time varies depending upon various factors. It is therefore desired to determine an optimum time depending upon the conditions. Generally, however, it is desired to complete the polymerization in 2 to 40 hours.

EXAMPLES

The present invention will be described in further detail by way of Examples, to which only, however, the invention is in no way limited.

Example 1

1.0 Gram (0.0028 mols) of a 5-hydroxy-(7H)benzo(c)fluorene derivative of the following formula,

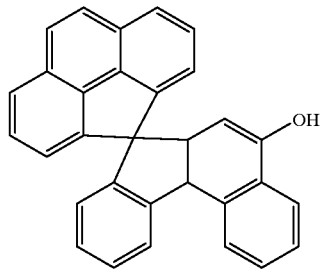

and 0.91 g (0.0031 mols) of a propargyl alcohol derivative of the following formula,

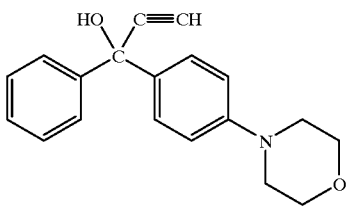

were dissolved in 50 ml of toluene, followed by the addition of 0.05 g of a p-toluenesulfonic acid. The mixture was stirred at room temperature for one hour. After the reaction, the solvent was removed, and the reaction product was refined by chromatography on silica-gel to obtain 0.4 g of a pale yellowish powdery product, yield 21%.

Elemental analysis of the product indicated C 88.10%, H 5.16%, N 2.04%, O 4.68%, which was in very good agreement with the calculated values C 88.08%, H 5.17%, N 2.06%, O 4.69% of $C_{50}H_{25}NO_2$.

Further, the proton nuclear magnetic resonance spectrum showed, as shown in FIG. 1, a peak of 8H due to methylene proton of a morpholino group near δ3.0 to 4.0 ppm and peaks of 27H due to aromatic protons and protons of alkenes near δ5.6 to 9.0 ppm.

Further, the $^{13}C$-nuclear magnetic resonance spectrum showed a peak due to carbon of an aromatic ring near δ110 to 160 ppm, a peak due to carbon of an alkene near δ80 to 140 ppm, and a peak due to carbon of an alkyl near δ20 to 60 ppm.

From the above results, it was confirmed that the isolated product was a compound represented by the following structural formula,

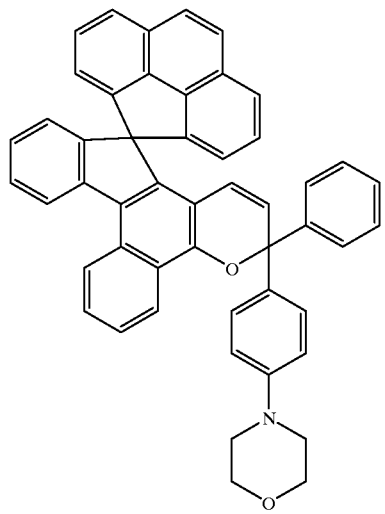

Examples 2 to 9

Chromene compounds shown in Tables 1 and 2 were synthesized in the same manner as in Example 1. The obtained products were analyzed for their structures relying on the same means for confirming the structure as that of Example 1, and it was confirmed that the compounds possessed structural formulas as shown in Tables 1 and 2. Table 3 shows elementally analyzed values of these compounds, calculated values found from the structural formulas of the compounds and characteristic spectra in the $^1H$-NMR spectra.

TABLE 1

| Example No. | Starting materials | | Products | Yields (%) |
|---|---|---|---|---|
| | Benzofluorene derivatives | Propargyl alcohol derivatives | | |
| 2 | | | | 25 |
| 3 | | | | 23 |

TABLE 1-continued
| Example No. | Starting materials | | Products | Yields (%) |
| --- | --- | --- | --- | --- |
| | Benzofluorene derivatives | Propargyl alcohol derivatives | | |
| 4 |  | 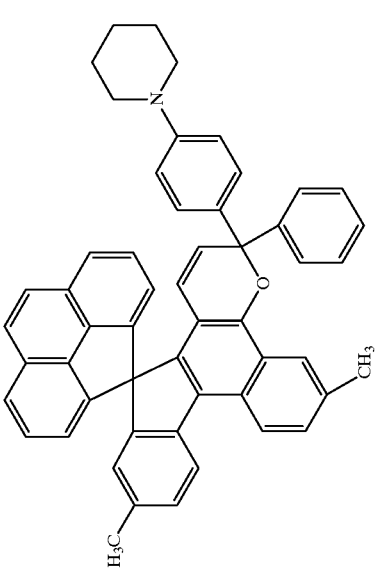 | 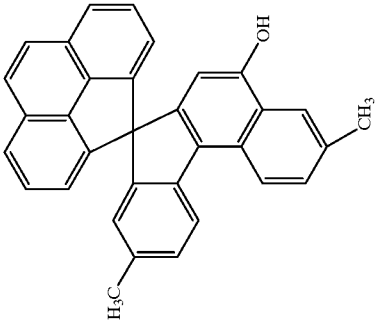 | 22 |
| 5 | 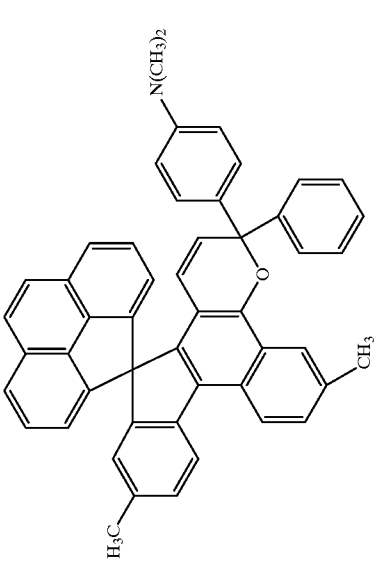 | 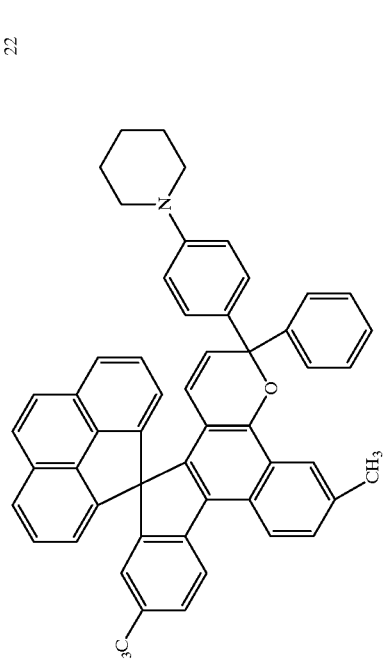 | 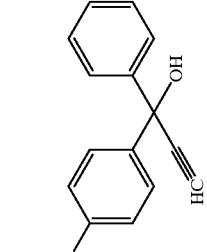 | 21 |

TABLE 2
| Example No. | Starting materials | | Products | Yields (%) |
| --- | --- | --- | --- | --- |
| | Benzofluorene derivatives | Propargyl alcohol derivatives | | |
| 6 | 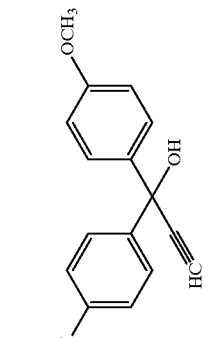 | 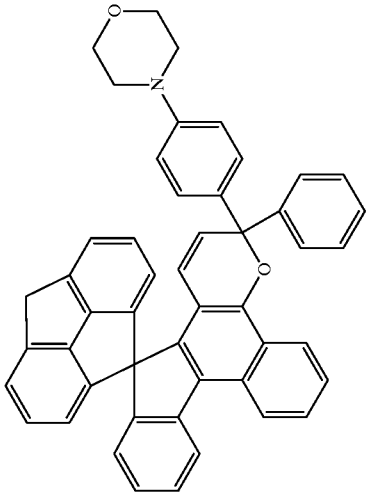 | 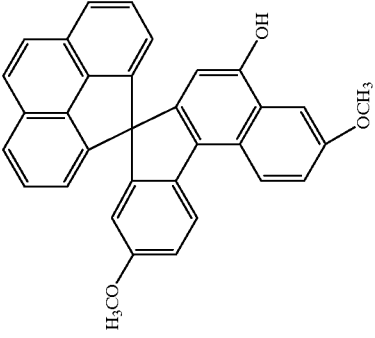 | 24 |
| 7 | 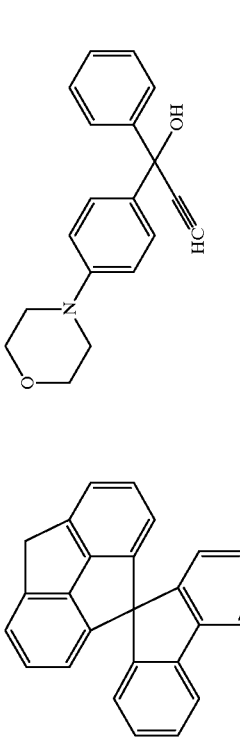 | 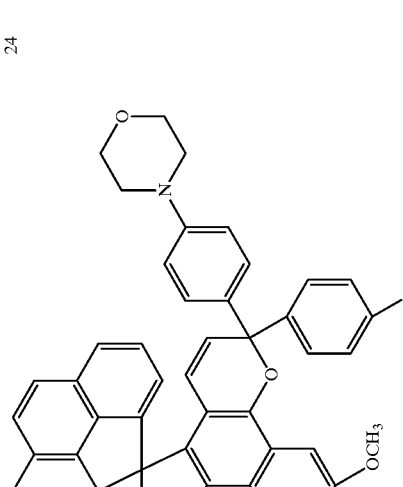 | 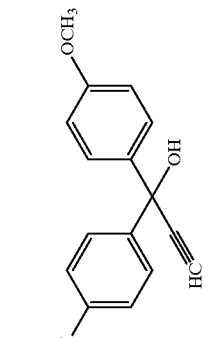 | 19 |

TABLE 2-continued

| Example No. | Starting materials | | Products | Yields (%) |
| --- | --- | --- | --- | --- |
| | Benzofluorene derivatives | Propargyl alcohol derivatives | | |
| 8 | | | | 12 |
| 9 | | | | 10 |

TABLE 3

| Example No. | Found C | H | N | O | others | Calculated C | H | N | O | others | ¹H—NMR (ppm) |
|---|---|---|---|---|---|---|---|---|---|---|---|
| 2 | 88.01 | 5.55 | 1.96 | 4.48 | | 87.98 | 5.54 | 1.97 | 4.51 | | δ5.6~9.0:25H<br>δ3.0~4.0:8H<br>δ1.5~2.5:6H |
| 3 | 86.07 | 5.26 | 1.95 | 6.72 | | 86.05 | 5.24 | 1.97 | 6.74 | | δ5.6~9.0:26H<br>δ3.0~4.0:11H |
| 4 | 89.95 | 5.86 | 1.96 | 2.23 | | 89.92 | 5.84 | 1.98 | 2.26 | | δ5.6~9.0:25H<br>δ3.0~4.0:4H<br>δ1.5~2.5:12H |
| 5 | 89.95 | 5.95 | 2.09 | 2.37 | | 89.92 | 5.58 | 2.10 | 2.40 | | δ5.6~9.0:25H<br>δ3.0~4.5:6H<br>δ1.0~3.0:6H |
| 6 | 82.49 | 5.37 | 1.79 | 10.34 | | 82.47 | 5.35 | 1.81 | 10.36 | | δ5.6~9.0:27H<br>δ4.0~4.5:14H |
| 7 | 87.89 | 5.29 | 2.07 | 4.75 | | 87.86 | 5.27 | 2.09 | 4.78 | | δ5.6~9.0:27H<br>δ3.0~4.5:8H |
| 8 | 86.11 | 4.88 | 2.03 | 7.00 | | 86.07 | 4.86 | 2.05 | 7.02 | | δ5.6~9.0:25H<br>δ3.0~4.5:8H |
| 9 | 90.95 | 5.06 | 1.88 | 2.13 | | 90.90 | 5.04 | 1.89 | 2.16 | | δ5.6~9.0:33H<br>δ1.8~4.5:4H |
| 11 | 87.61 | 4.81 | | 2.52 | S5.06 | 87.59 | 4.79 | | 2.54 | S5.08 | δ5.6~9.5:24H<br>δ1.0~3.0:6H |
| 12 | 87.80 | 5.65 | 1.99 | 4.56 | | 87.77 | 5.63 | 2.01 | 4.59 | | δ5.6~9.0:23H<br>δ3.0~4.5:4H<br>δ1.0~2.5:12H |
| 13 | 85.60 | 5.26 | 2.06 | 7.10 | | 85.56 | 5.24 | 2.08 | 7.12 | | δ5.6~9.0:24H<br>δ2.8~4.5:11H |
| 14 | 84.25 | 5.49 | 1.83 | 8.45 | | 84.21 | 5.47 | 1.85 | 8.47 | | δ5.6~9.0:23H<br>δ2.8~4.5:18H |
| 15 | 84.22 | 5.32 | 1.87 | 8.60 | | 84.19 | 5.30 | 1.89 | 8.63 | | δ5.6~9.0:25H<br>δ3.0~4.5:14H |
| 16 | 83.82 | 5.08 | | 11.10 | | 83.78 | 5.06 | | 11.16 | | δ5.6~9.0:24H<br>δ2.8~4.5:12H |
| 17 | 84.62 | 5.54 | 3.64 | 6.23 | | 84.57 | 5.52 | 3.65 | 6.26 | | δ5.6~9.0:26H<br>δ3.0~4.5:16H |
| 18 | 85.86 | 4.92 | 1.97 | 4.55 | F2.69 | 85.81 | 4.90 | 2.00 | 4.57 | F2.71 | δ5.6~9.5:26H<br>δ3.0~4.5:8H |

Example 10

1.0 Gram (0.0018 mols) of the precursor chromene compound 1 of the following formula,

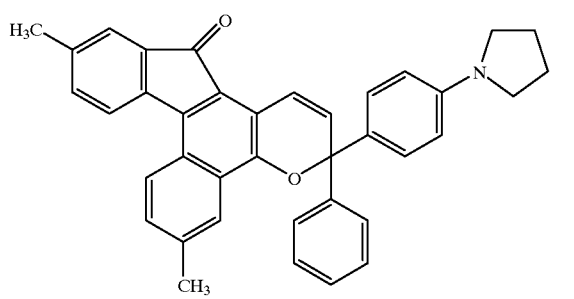

dissolved in 30 ml of a tetrahydrofuran was added while maintaining a temperature of 25° C. to 0.63 g (0.0023 mols) of the Grignard reagent of the following formula,

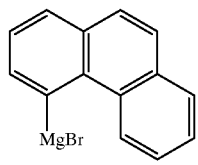

diluted with 20 ml of the tetrahydrofuran, and was reacted for one hour. After the reaction, the reaction solution was poured into the water, neutralized with an aqueous solution of 10% of hydrochloric acid and, then, the organic layer was separated. The obtained organic layer was then washed with water and, then, with a saturated saline solution. Thereafter, the solvent was removed to obtain a residue. To the residue were added 30 ml of acetic acid and 2 ml of concentrated hydrochloric acid, and the mixture was heated at 70° C. for 30 minutes. The reaction solution was poured into the water, neutralized with an aqueous solution containing sodium hydroxide, extracted with tetrahydrofuran, washed with the water and was washed with the saturated saline solution. Then, the solvent was removed, and the reaction product was refined by chromatography on silica-gel to obtain 0.2 g of a pale yellowish powdery product, yield 13.3%. Elemental analysis of the product indicated C 90.20%, H 5.24%, N 2.13%, O 2.43%, which was in very good agreement with the calculated values C 90.15%, H 5.25%, N 2.15%, O 2.45% of $C_{49}H_{34}NO$. Further, the proton nuclear magnetic resonance spectrum showed a peak of 4H due to methylene proton of a pyrrolidino group near δ1.5 to 2.0 ppm, a peak of 4H due to methylene proton of the pyrrolidino group near δ3.0 to 4.0 ppm, and a peak of 26H due to aromatic protons and protons of alkenes near δ5.6 to 9.0 ppm.

Further, the $^{13}C$-nuclear magnetic resonance spectrum showed a peak due to carbon of an aromatic ring near δ110 to 160 ppm, a peak due to carbon of an alkene near δ80 to 140 ppm, and a peak due to carbon of an alkyl near δ20 to 60 ppm.

From the above results, it was confirmed that the isolated product was a compound represented by the following structural formula,

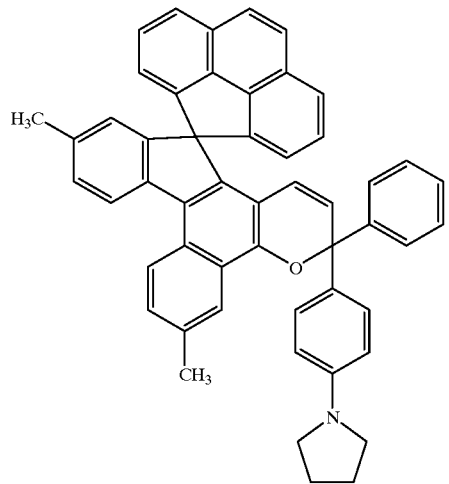

Examples 11 to 18

Chromene compounds shown in Tables 4 and 5 were synthesized in the same manner as in Example 10. The obtained products were analyzed for their structures relying on the same means for confirming the structure as that of Example 1, and it was confirmed that the compounds possessed structural formulas as shown in Tables 4 and 5. Table 3 shows elementally analyzed values of these compounds, calculated values found from the structural formulas of the compounds and characteristic spectra in the $^1H$-NMR spectra.

TABLE 4

| Example No. | Starting materials | | Products | Yields (%) |
|---|---|---|---|---|
| | Precusor chromene compounds 1 | Grignard reagents | | |
| 11 | [structure] | [structure] | [structure] | 8 |
| 12 | [structure] | [structure] | [structure] | 5 |

TABLE 4-continued

| Example No. | Starting materials | | Products | Yields (%) |
|---|---|---|---|---|
| | Precursor chromene compounds 1 | Grignard reagents | | |
| 13 | (structure) | (structure) | (structure) | 4 |
| 14 | (structure) | (structure) | (structure) | 4 |

TABLE 5

| Example No. | Starting materials | | Products | Yields (%) |
|---|---|---|---|---|
| | Precursor chromene compounds 1 | Grignard reagents | | |
| 15 | [structure] | [structure] | [structure] | 8 |
| 16 | [structure] | [structure] | [structure] | 5 |

TABLE 5-continued

| Example No. | Starting materials | | Products | Yields (%) |
|---|---|---|---|---|
| | Precursor chromene compounds 1 | Grignard reagents | | |
| 17 | [structure] | [structure] MgBr | [structure] | 4 |
| 18 | [structure] | [structure] MgBr | [structure] | 4 |

Examples 19 to 36

0.05 Parts of the chromene compound obtained in Example 1 was added to 70 parts (Here, "parts" means "parts by weight".) of a nonaethylene glycol dimethacrylate, 15 parts of a triethylene glycol dimethacrylate, 10 parts of a glycidyl methacrylate and 5 parts of a 2-hydroxyethyl methacrylate and 1.5 parts of perbutyl ND (manufactured by by NOF corp.), and was mixed to a sufficient degree. The mixture solution was poured into a mold constituted by glass plates and gaskets of an ethylene/vinyl acetate copolymer, and was cast-polymerized. The polymerization was conducted by using an air furnace while gradually elevating the temperature from 30° C. up to 90° C. over 18 hours, and was maintained at 90° C. for 2 hours. After the polymerization, the polymer was removed from the glass mold.

The thus obtained polymer (sample) having a thickness of 2 mm was irradiated with light from a xenon lamp L-2480 (300 W) SHL-100 manufactured by Hamamatsu Photonics Co. through an Aeromass filter (manufactured by Coning Co.) at 20° C.±1° C. at beam intensities on the polymer surface of 2.4 mW/cm$^2$ (at the wavelength of 365 nm and 24 µW/cm$^2$ (at the wavelength of 245 nm) for 120 seconds to develop a color, in order to measure the photochromic properties of the sample. The photochromic properties were evaluated in a manner as described below.

① Maximum absorption wavelength (λmax): A maximum absorption wavelength after the color is developed as found by using a spectrophotometer (instantaneous multichannel photo detector MCPD 1000) manufactured by Otsuka Denshi Kogyo Co. The maximum absorption wavelength is related to a color tone of when the color is developed.

② Initial color {ε(0)}: Absorbancy at the maximum absorption wavelength in a state of not being irradiated with light. In an optical material such as lenses of spectacles, it can be said that the lower this value is, the more excellent the photochromic property is.

③ Color density {ε(120)−ε(0)}: A difference between ε(0) and the absorbancy {ε(120)} after irradiated with light having the maximum absorption wavelength for 120 seconds. It can be said that the higher this value is, the more excellent the photochromic property is.

④ Color-developing sensitivity (sec): Time until the absorbency of the sample at the maximum wavelength reaches its saturation by the irradiation with light. It can be said that the shorter the time is, the more excellent the color-developing sensitivity is.

⑤ Fading rate [t1/2(min)]: Time until the absorbancy of the sample at the maximum wavelength drops to one-half of {ε(120)−ε(0)} when the irradiation with light is discontinued after irradiated with light for 120 seconds. It can be said that the shorter the time is, the more excellent the photochromic property is.

⑥ Remaining ratio (%)={($A_{200}$/$A_0$)×100}: The following deterioration promotion testing was conducted in order to evaluate the light resistance of color developed upon being irradiated with light. That is, deterioration of the obtained polymer (sample) was promoted by using a xenon wheatherometer X25 manufactured by Suga Shikenki Co. for 200 hours. Thereafter, the color density was evaluated before and after the testing; i.e., the color density ($A_0$) of before the testing and the color density ($A_{200}$) of after the testing were measured, and a value {($A_{200}$/$A_0$)×100} was regarded as a remaining ratio (%) and was used as an index of light resistance of the developed color. The higher the remaining ratio is, the higher the light resistance of the developed color is.

⑦ Degree of change in the developed color (ΔYI)=YI(200)−YI(0): In order to evaluate the durability of color tone of when not irradiated with light, the samples of before and after the deterioration promotion testing were measured for their color difference by using a color-difference meter (SM-4) manufactured by Suga Shikenki Co. A change in the color due to deterioration was found, i.e., a difference {ΔYI} was found by subtracting a value {YI(0)} of the coloring degree of before the testing from a value {YI(200)} of the coloring degree of after the testing (after 200 hours), in order to evaluate the durability. The smaller the ΔYI, the higher the durability of color tone of when not irradiated with light.

Further, the photochromic polymers were obtained in the same manner as described above but using the chromene compounds of Examples 2 to 18, and their properties were evaluated. The results were as shown in Table 6.

TABLE 6

| Example No. | Compound No. | λmax (nm) | Initial color ε(0) | Color density ε(120) − ε(0) | Color-developing sensitivity (sec.) | Fading rate τ ½ (min.) | Durability ΔYI | Remaining ratio |
|---|---|---|---|---|---|---|---|---|
| 19 | 1 | 470 | 0.03 | 0.90 | 50 | 2.0 | 1.5 | 95 |
|    |   | 570 | 0.03 | 1.30 | 50 | 2.0 |     | 95 |
| 20 | 2 | 474 | 0.03 | 1.00 | 42 | 2.0 | 1.5 | 95 |
|    |   | 578 | 0.03 | 1.30 | 42 | 2.0 |     | 95 |
| 21 | 3 | 474 | 0.04 | 0.85 | 60 | 1.8 | 2   | 94 |
|    |   | 578 | 0.04 | 1.25 | 60 | 1.8 |     | 94 |
| 22 | 4 | 474 | 0.04 | 1.20 | 43 | 2.0 | 2.6 | 94 |
|    |   | 584 | 0.04 | 0.80 | 43 | 2.0 |     | 94 |

TABLE 6-continued

| Example No. | Compound No. | λmax (nm) | Initial color ε (0) | Color density ε (120) − ε (0) | Color-developing sensitivity (sec.) | Fading rate τ ½ (min.) | Durability ΔYI | Remaining ratio |
|---|---|---|---|---|---|---|---|---|
| 23 | 5 | 485 | 0.04 | 0.80 | 42 | 1.6 | 2.5 | 93 |
|  |  | 592 | 0.04 | 1.10 | 42 | 1.6 |  | 93 |
| 24 | 6 | 476 | 0.03 | 0.78 | 40 | 1.8 | 2.0 | 94 |
|  |  | 582 | 0.03 | 1.20 | 40 | 1.8 |  | 94 |
| 25 | 7 | 470 | 0.04 | 0.92 | 55 | 2.0 | 2.0 | 93 |
|  |  | 572 | 0.03 | 1.22 | 55 | 2.0 |  | 93 |
| 26 | 8 | 470 | 0.05 | 1.00 | 60 | 2.1 | 3.0 | 92 |
|  |  | 574 | 0.03 | 0.90 | 60 | 2.1 |  | 92 |
| 27 | 9 | 476 | 0.03 | 0.95 | 60 | 2.2 | 2.0 | 93 |
|  |  | 585 | 0.03 | 1.30 | 60 | 2.2 |  | 93 |
| 28 | 10 | 490 | 0.04 | 0.82 | 60 | 1.7 | 3.0 | 92 |
|  |  | 600 | 0.04 | 1.12 | 60 | 1.7 |  | 92 |
| 29 | 11 | 465 | 0.04 | 0.70 | 45 | 3.2 | 3.0 | 92 |
|  |  | 565 | 0.04 | 0.80 | 45 | 3.2 |  | 92 |
| 30 | 12 | 482 | 0.04 | 1.00 | 48 | 2.0 | 2.0 | 94 |
|  |  | 584 | 0.04 | 1.40 | 48 | 2.0 |  | 94 |
| 31 | 13 | 485 | 0.04 | 0.80 | 60 | 1.8 | 2.0 | 93 |
|  |  | 590 | 0.04 | 1.05 | 60 | 1.8 |  | 93 |
| 32 | 14 | 474 | 0.04 | 1.00 | 48 | 2.0 | 2.0 | 94 |
|  |  | 580 | 0.04 | 1.35 | 48 | 2.0 |  | 94 |
| 33 | 15 | 480 | 0.04 | 0.92 | 40 | 1.7 | 2.0 | 94 |
|  |  | 614 | 0.04 | 1.55 | 40 | 1.7 |  | 95 |
| 34 | 16 | 470 | 0.04 | 1.00 | 45 | 1.1 | 1.5 | 95 |
|  |  | 580 | 0.04 | 1.60 | 45 | 0.9 |  | 95 |
| 35 | 17 | 484 | 0.04 | 0.70 | 60 | 0.7 | 2.4 | 92 |
|  |  | 616 | 0.04 | 0.84 | 60 | 0.5 |  | 92 |
| 36 | 18 | 472 | 0.04 | 0.52 | 50 | 0.3 | 1.0 | 96 |
|  |  | 574 | 0.04 | 0.78 | 50 | 0.2 |  | 96 |

Examples 37 to 40

0.05 Parts of the chromene compounds listed on the Table 7 were added to 80 parts of nonaethylene glycol dimethacrylate, 10 parts of tetraethylene glycol dimethacrylate, 3 parts of triethylene glycol dimethacrylate, 5 parts of glycidyl methacrylate, 2 parts of 2-hydroxyethylmethacrylate and 1 part of perbutyl ND, and mixed to sufficient degree. Thereafter the photochromic polymers were obtained by using the mixture solution on the same polymerization condition of example 19, and their properties were evaluated. The results were as shown in Table 7.

Comparative Examples 1 to 7

Photochromic polymers were obtained in the same manner as in Example 19 but using the compounds represented by the following formulas (A) to (G), and their properties were evaluated. The results were as shown in Table 8.

The compound of the formula (A) is the chromene compound disclosed in International Patent Publication WO96/14596, the compound of the formula (B) is the chromene compound disclosed in International Patent Publication WO97/48762, and the compounds of the formulas (C) to (E) are chromene compound disclosed in Examples 4, 7 and 5 of German Patent Application Publication DE 19902771 A1. The compounds of the formulas (G) and (F) are those obtained in the stage of study by the present inventors.

TABLE 7

| Example No. | Compound No. | λmax (nm) | Initial color ε (0) | Color density ε (120) − ε (0) | Color-developing sensitivity (sec.) | Fading rate τ 1/2 (min.) | Durability ΔYI | Remaining ratio |
|---|---|---|---|---|---|---|---|---|
| 37 | 1 | 472 | 0.03 | 0.90 | 46 | 1.8 | 1.6 | 94 |
|  |  | 572 | 0.03 | 1.31 | 46 | 1.8 |  | 93 |
| 38 | 3 | 476 | 0.03 | 0.86 | 55 | 1.7 | 2.0 | 94 |
|  |  | 582 | 0.03 | 1.30 | 55 | 1.7 |  | 94 |
| 39 | 15 | 480 | 0.04 | 0.94 | 40 | 1.7 | 2.0 | 93 |
|  |  | 614 | 0.04 | 1.56 | 40 | 1.7 |  | 93 |
| 40 | 16 | 470 | 0.04 | 1.00 | 45 | 1.0 | 1.7 | 94 |
|  |  | 582 | 0.04 | 1.62 | 45 | 1.0 |  | 94 |

Comparative Example 4
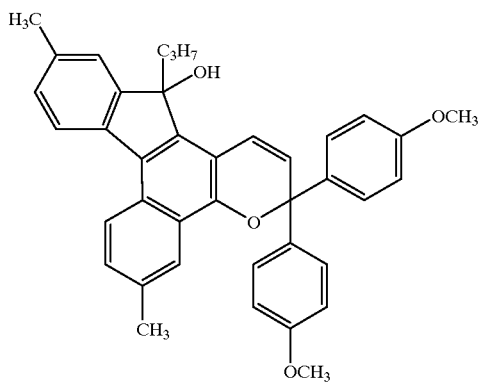
(A)
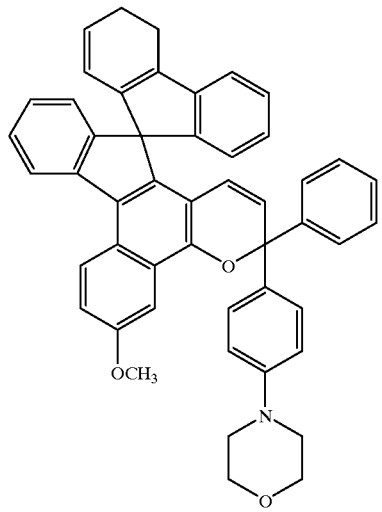
(D)
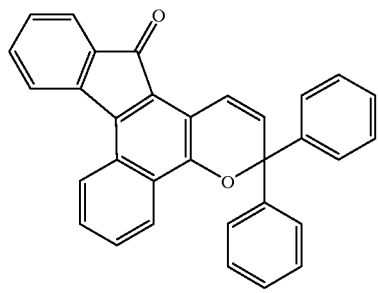
(B)
Comparative Example 5
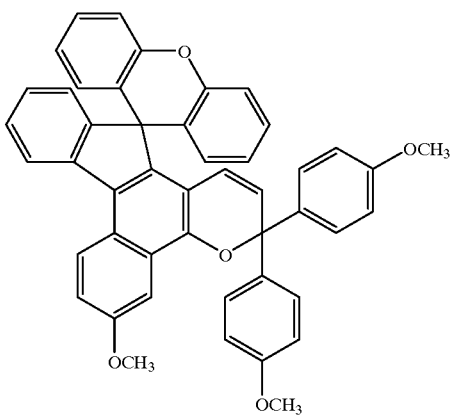
(E)
Comparative Example 3
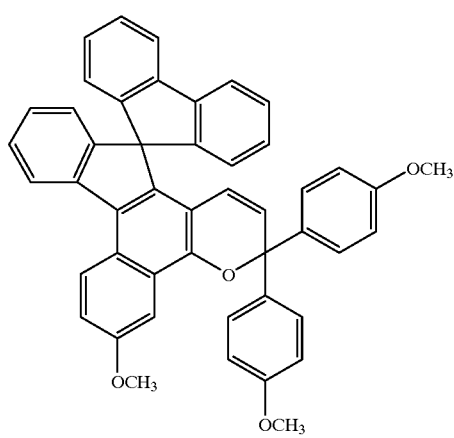
(C)
Comparative Example 6
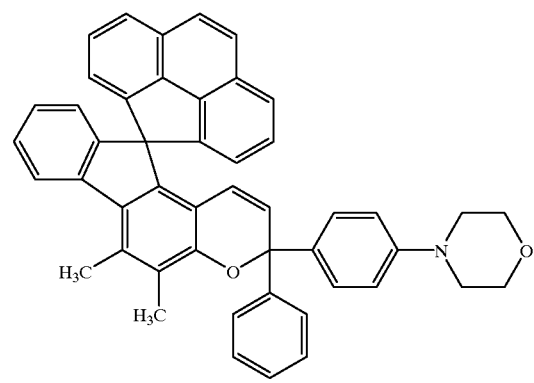
(F)

Comparative Example 7

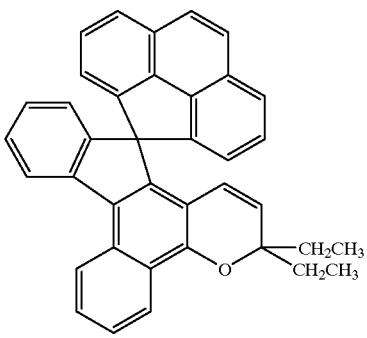

(G)

TABLE 8

| Comparative Example No. | Compound No. | λ max (nm) | Initial color ε (0) | Color density ε (120) − ε(0) | Color = developing sensitivity (sec.) | Fading rate τ 1/2 (min.) | Durability ΔYI | Remaining ratio |
|---|---|---|---|---|---|---|---|---|
| 1 | (A) | 440 | 0.03 | 0.40 | 125 | 10.0 | 8 | 73 |
|   |     | 570 | 0.03 | 0.5  | 125 | 10.0 |   | 73 |
| 2 | (B) | 425 | 0.05 | 0.20 | 150 | 15.0 | 15 | 70 |
|   |     | 536 | 0.03 | 0.3  | 150 | 15.0 |   | 70 |
| 3 | (C) | 460 | 0.03 | 0.70 | 140 | 5.0  | 3 | 90 |
|   |     | 575 | 0.03 | 1.1  | 140 | 5.0  |   | 90 |
| 4 | (D) | 470 | 0.03 | 0.70 | 125 | 3.0  | 3 | 70 |
|   |     | 580 | 0.03 | 1.1  | 125 | 3.0  |   | 70 |
| 5 | (E) | 460 | 0.03 | 0.60 | 160 | 4.0  | 4 | 80 |
|   |     | 576 | 0.03 | 1    | 160 | 4.0  |   | 80 |
| 6 | (F) | 440 | 0.01 | 0.04 | 60  | 0.5  | 15 | 20 |
|   |     | 525 | 0.01 | 0.06 | 60  | 0.5  |   | 20 |
| 7 | (G) | 460 | 0.03 | 0.10 | 180 | 5.5  | 5 | 5 |
|   |     | 540 | 0.03 | 0.5  | 180 | 5.5  |   | 5 |

In Examples 19 to 36 using the chromene compounds of the present invention, the photochromic polymers are superior to those of Comparative Examples 1 to 7 concerning every respect, i.e., exhibit high color-developing sensitivities, high fading rates, less color after aged and good durability.

The chromene compounds (Comparative Examples 3 to 5) having structures similar to that of the chromene compound of the present invention, exhibit poor fading rates and color-developing sensitivities compared to those of the chromene compound of the present invention since the group that is spiro-bonded to the indene ring in the above-mentioned general formula (1) does not have a group represented by —X— specified by the present invention.

Despite the group spiro-bonded to the indene ring has the group represented by —X—, the chromene compound (Comparative Example 6) exhibits a high fading rate but very low color density and durability (remaining ratio) when divalent groups are not bonded to carbon atoms at the fifth and sixth positions of the chromene ring to form a ring. Concerning the color-developing sensitivity, this compound is inferior to the chromene compound of the present invention. When substituents other than those of $R^3$ and $R^4$ of the above-mentioned general formula (1) are bonded to the carbon atom at the second position of the chromene ring (Comparative Example 7), the chromene compound exhibits a fading rate, a color-developing sensitivity and a color density which are inferior to those of the chromene compound of the present invention and, besides, exhibits a very low durability (remaining ratio).

As will be understood from the above detailed description, the chromene compound of the present invention exhibits excellent photochromic properties such as small initial color, high color density, superior durability, as well as high color-developing sensitivity and high fading rate even when the chromene compound is dispersed in a solution or in a high-molecular solid matrix.

Therefore, a photochromic lens prepared by using the chromene compound of the invention quickly develops a dense color when a person carries it outdoors, and quickly returns to its initial color tone when the person carries it back indoors since the color fades quickly. Besides, the photochromic lens exhibits a high durability even after it is used for extended periods of time.

What is claimed is:

1. A chromene compound represented by the formula (1),

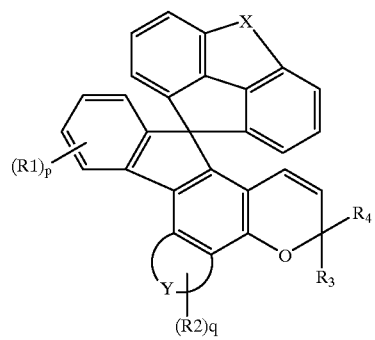

(1)

wherein,
$R^1$ is an alkyl group, an alkoxy group, an aralkoxy group, an amino group, a substituted amino group, a cyano group, a substituted or unsubstituted aryl group, a halogen atom, an aralkyl group, a monovalent substituted or unsubstituted heterocyclic group having a nitrogen atom as a hetero atom and bonded to the indene ring through the nitrogen atom, or a monovalent condensed heterocyclic group in which said heterocyclic group is condensed with an aromatic hydrocarbon ring or an aromatic heterocyclic ring, and p is an integer of from 0 to 3;

a divalent group represented by the following formula (2),

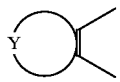

(2)

is an aromatic hydrocarbon group or an unsaturated heterocyclic ring;

$R^2$ is an alkyl group, an alkoxy group, an aralkoxy group, an amino group, a substituted amino group, a cyano group, a substituted or unsubstituted aryl group, a halogen atom, an aralkyl group, a monovalent substituted or unsubstituted heterocyclic group having a nitrogen atom as a hetero atom and is bonded to the ring of the group represented by the above formula (2) through the nitrogen atom, or a monovalent condensed heterocyclic group in which said heterocyclic group is condensed with an aromatic hydrocarbon ring or an aromatic heterocyclic ring, and q is an integer of from 0 to 3;

$R^3$ and $R^4$, independently from each other, represent a group of formula (3), formula (4), substituted or unsubstituted aryl group, or substituted or unsubstituted heteroaryl group;

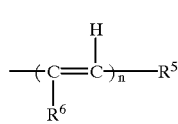

(3)

wherein $R^5$ is a substituted or unsubstituted aryl group, or a substituted or unsubstituted heteroaryl group, $R^6$ is a hydrogen atom, an alkyl group or a halogen atom, and n is an integer of from 1 to 3;

(4)

wherein $R^7$ is a substituted or unsubstituted aryl group, or a substituted or unsubstituted heteroaryl group, and m is an integer of from 1 to 3; or $R^3$ and $R^4$ are groups which together form an aliphatic hydrocarbon ring or an aromatic hydrocarbon ring; and X is represented by one of the following formula,

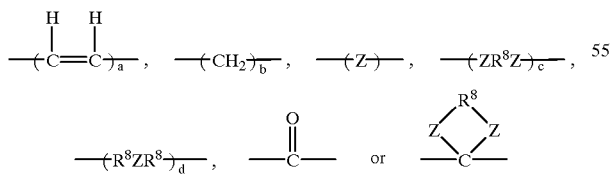

wherein Z is an oxygen atom or a sulfur atom, $R^8$ is an alkylene group with 1 to 6 carbon atoms, and a, b, c and d are, independently of each other, integers of from 1 to 4.

2. A chromene compound represented by the following general formula (6),

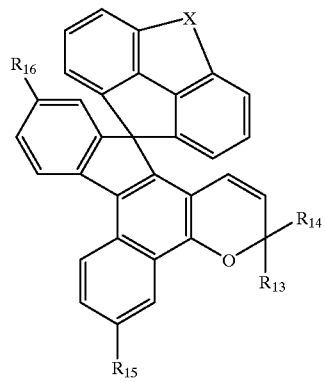

(6)

wherein $R^{15}$ and $R^{16}$ are, independently from each other, alkyl group with 1 to 4 carbon atoms, alkoxy group with 1 to 5 carbon atoms, aralkoxy group with 6 to 10 carbon atoms, mono-substituted or di-substituted amino group having, as a substituent, an aralkyl group with 1 to 4 carbon atoms or an aryl group with 6 to 10 carbon atoms, cyano group, aryl group with 6 to 10 carbon atoms, substituted aryl group with 6 to 10 carbon atoms (without including carbon atoms of a substituent) substituted with an alkyl group having 1 to 4 carbon atoms or an alkoxy group having 1 to 5 carbon atoms, halogen atom, or substituted or unsubstituted heterocyclic group having a nitrogen atom as a hetero atom being bonded to the indene ring or the naphthalene ring through the nitrogen atom and being selected from morpholino group, piperidino group, pyrrolidinyl group, 1-piperazinyl group, 4-methyl-1-piperazinyl group or indolinyl group, or condensed heterocyclic group in which said heterocyclic group is condensed with an aromatic hydrocarbon ring or an aromatic heterocyclic ring;

at least either one of $R^{13}$ and $R^{14}$ is a substituted aryl group with 6 to 10 carbon atoms (without including carbon atoms of a substituent) having at least one substituent selected from a mono-substituted or di-substituted amino group having, as a substituent, an alkyl group with 1 to 4 carbon atoms or an aryl group with 6 to 10 carbon atoms, alkoxy group with 1 to 5 carbon atoms, morpholino group, piperidino group, pyrrolidinyl group, 1-piperazinyl group, 4-methyl-1-piperazinyl group and indolinyl group, or a heteroaryl group with 4 to 12 carbon atoms (without including carbon atoms of a substituent);

and X is a divalent group represented by —CH=CH—.

3. A chromene compound according to claim 2, wherein:

$R^{15}$ and $R^{16}$ are, independently from each other, alkyl group with 1 to 4 carbon atoms, alkoxy group with 1 to 5 carbon atoms, halogen atom, or morpholino group;

at least either one of $R^{13}$ and $R^{14}$ is an aryl group with 6 to 10 carbon atoms substituted with at least one substituent selected from the group consisting of (i) mono-substituted or di-substituted amino group having, as a substituent, an alkyl group with 1 to 4 carbon atoms or an aryl group with 6 to 10 carbon atoms, (ii) alkoxy group with 1 to 5 carbon atoms, (iii) morpholino group, (iv) piperidino group, (v) pyrrolidinyl group, (vi) 1-piperazinyl group, (vii) 4-methyl-1-piperazinyl group and (viii) indolinyl group; and when either one of $R^{13}$ and $R^{14}$ is not the above group, the other one is an aryl group with 6 to 10 carbon atoms, or a heteroaryl group with 4 to 12 carbon atoms.

4. A chromene compound according to claim 3, wherein $R^{15}$ and $R^{16}$ are methyl group or methoxyl group, either one of $R^{13}$ and $R^{14}$ is a phenyl group having a piperidino group, a morpholino group or a methoxyl group as a substituent, and the other one thereof is a phenyl group or a methoxyphenyl group.

5. A photochromic material comprising a chromene compound of claim 1 or claim 2.

6. A photochromic optical material containing a chromene compound of claim 1 or claim 2.

7. A photochromic polymerizable composition containing a chromene compound of claim 1 or claim 2, and a polymerizable monomer.

8. A photochromic polymerizable composition according to claim 7, further comprising a polymerization initiator.

9. A photochromic polymerizable composition according to claim 8, wherein said polymerizable monomer comprises a (meth)acrylic acid ester compound.

10. A photochromic polymerizable composition according to claim 7, wherein said polymerizable monomer comprises a (meth)acrylic acid ester compound.

11. A chromene compound having a formula selected from the group consisting of:

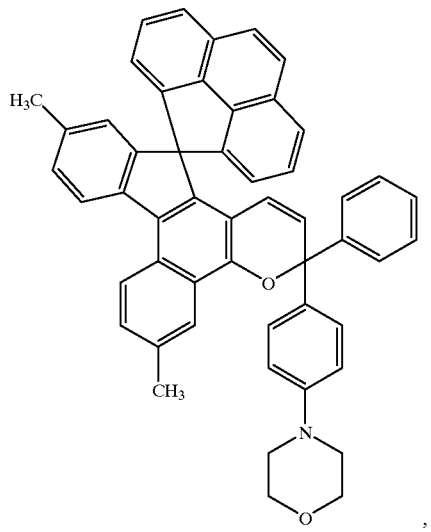

,

-continued

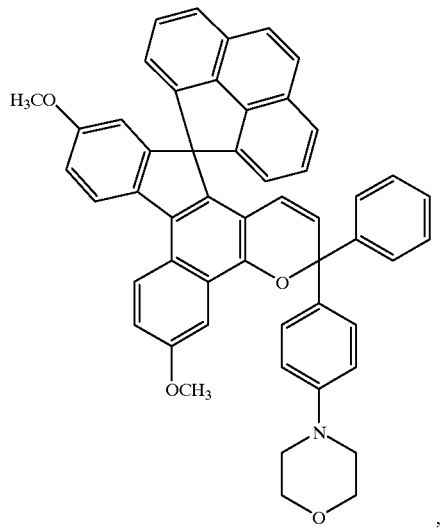

,

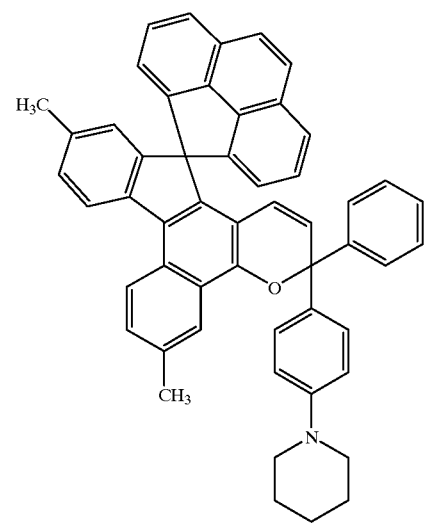

,

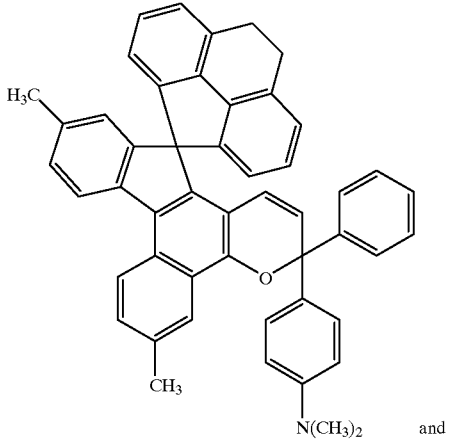

and

-continued
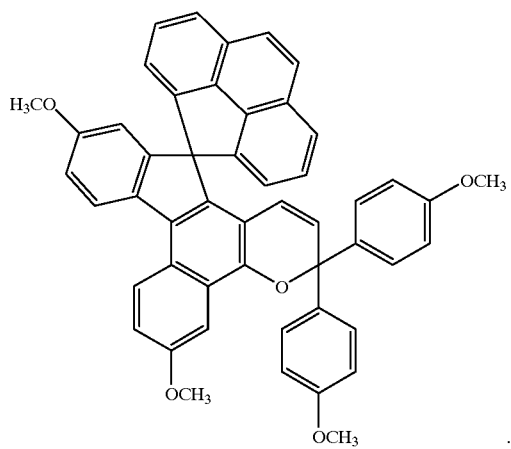
12. A chromene compound having a formula selected from the group consisting of:
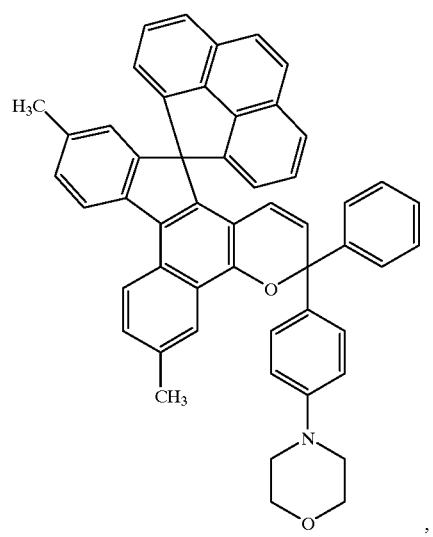
,
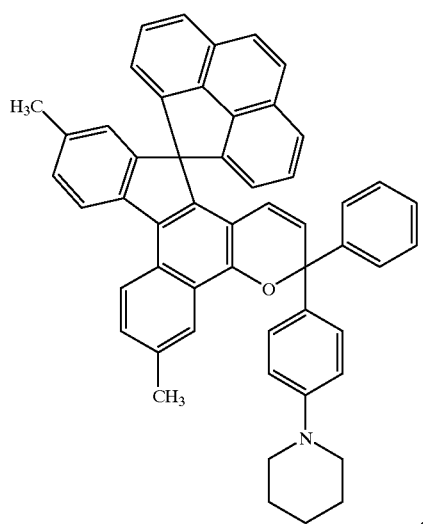
and
-continued
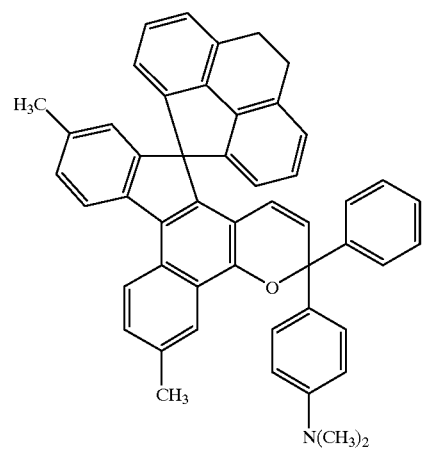
13. A chromene compound having a formula selected from the group consisting of:
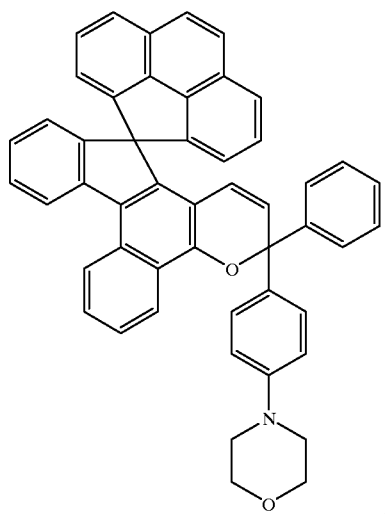
,
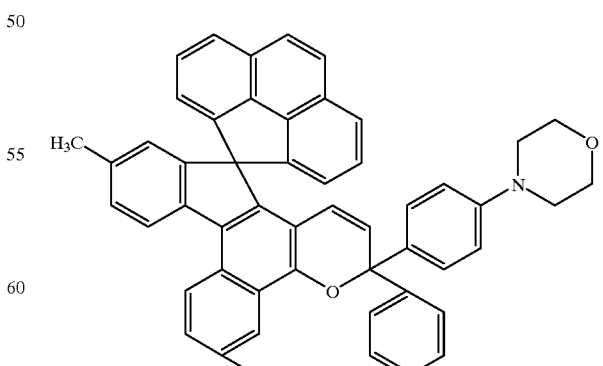
,

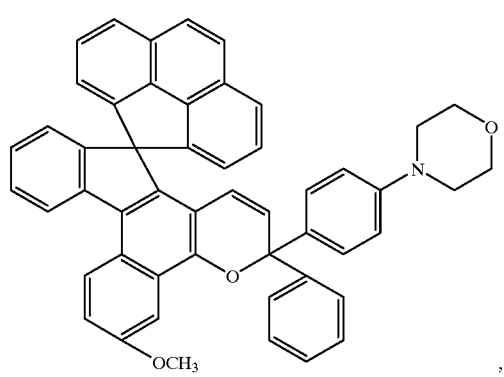
,
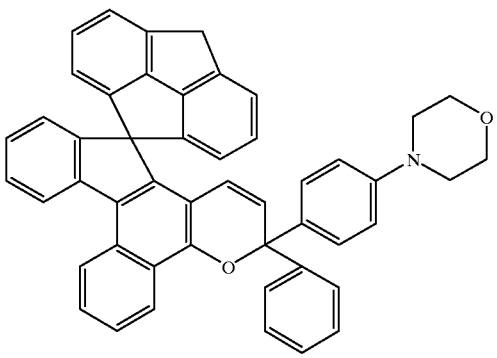
,
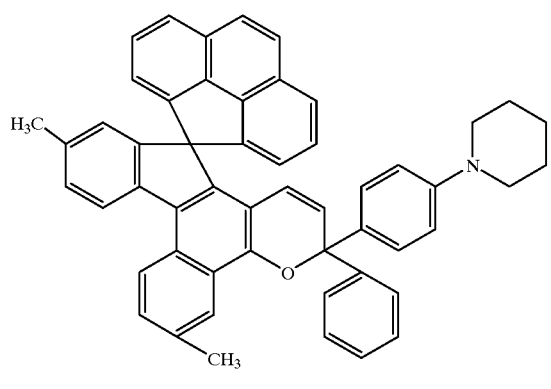
,
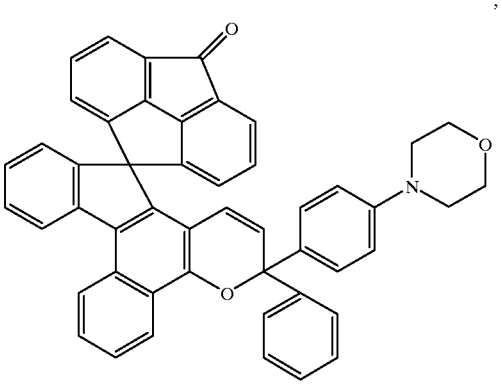
,
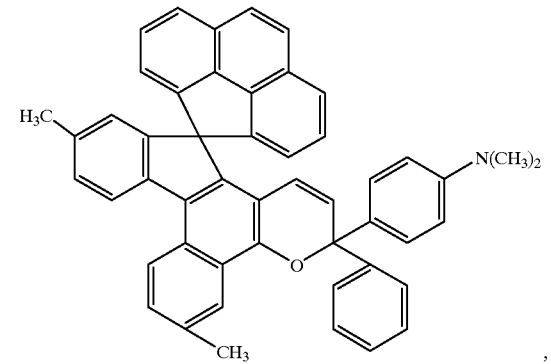
,
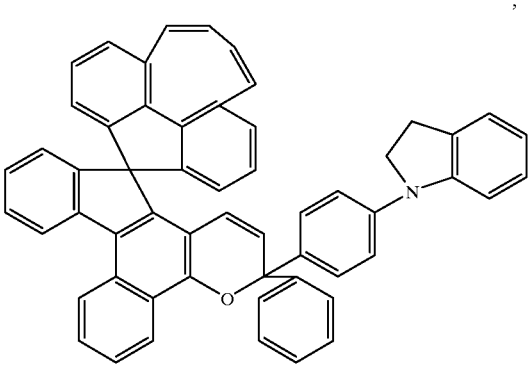
,
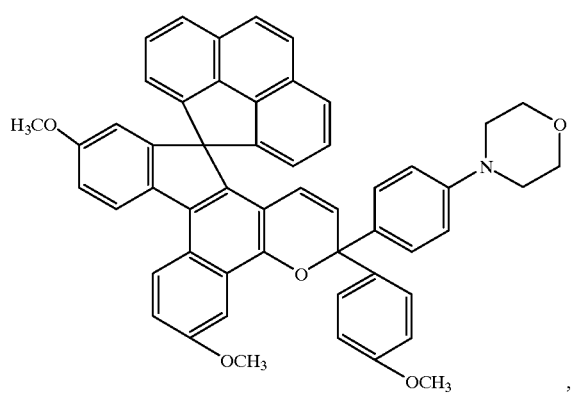
,
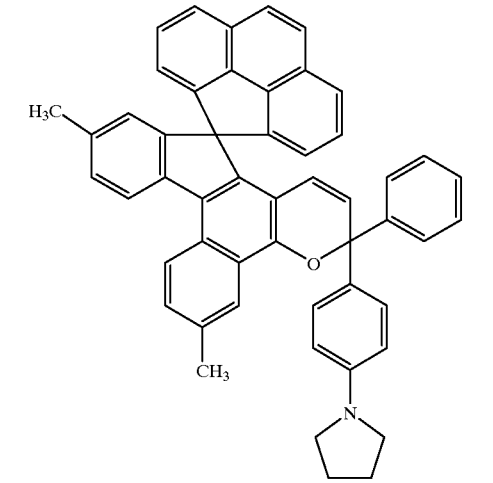
,

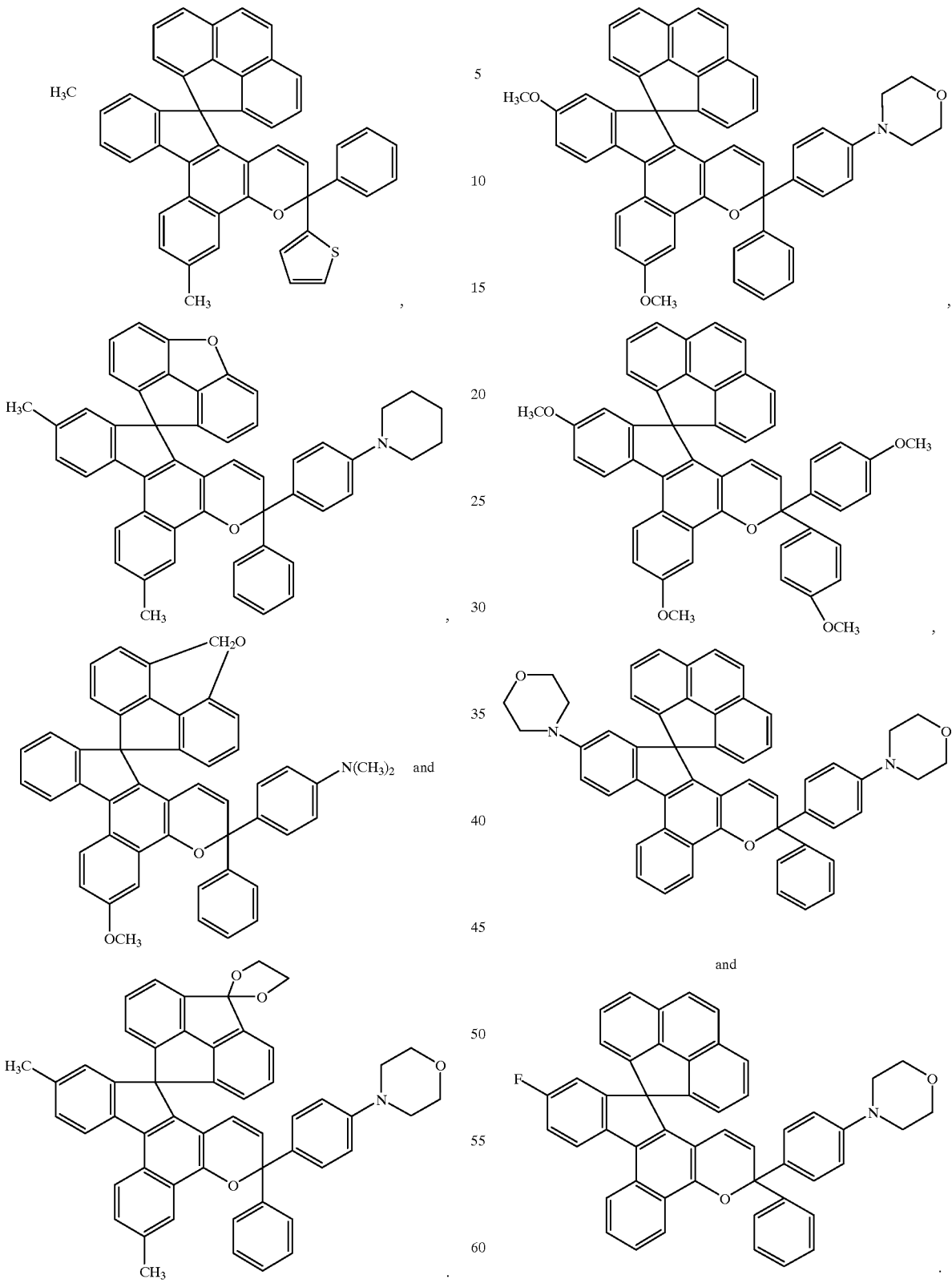
14. A chromene compound having a formula selected from the group consisting of:
15. A chromene compound represented by the formula (1),

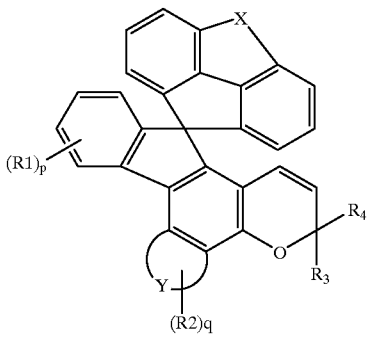

(1)

wherein, $R^1$ is an hydroxyl group, a nitro group, a trifluoromethyl group or a monovalent heterocyclic group bonded to the indene ring through the carbon atom, and p is an integer of from 0 to 3;

a divalent group represented by the following formula (2),

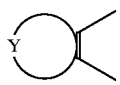

(2)

is an aromatic hydrocarbon group or an unsaturated heterocyclic ring;

$R^2$ is an hydroxy group, a nitro group, a trifluoromethyl group, or a monovalent heterocyclic group bonded to the ring of the group represented by the above formula (2) through the carbon atom, and q is an integer of from 0 to 3;

$R^3$ and $R^4$, independently from each other, represent a group of formula (3), formula (4), substituted or unsubstituted aryl group, or substituted or unsubstituted heteroaryl group;

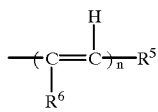

(3)

wherein $R^5$ is a substituted or unsubstituted aryl group, or a substituted or unsubstituted heteroaryl group, $R^6$ is a hydrogen atom, an alkyl group or a halogen atom, and n is an integer of from 1 to 3;

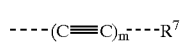

(4)

wherein $R^7$ is a substituted or unsubstituted aryl group, or a substituted or unsubstituted heteroaryl group, and m is an integer of from 1 to 3; or $R^3$ and $R^4$ are groups which together form an aliphatic hydrocarbon ring or an aromatic hydrocarbon ring; and X is represented by one of the following formula,

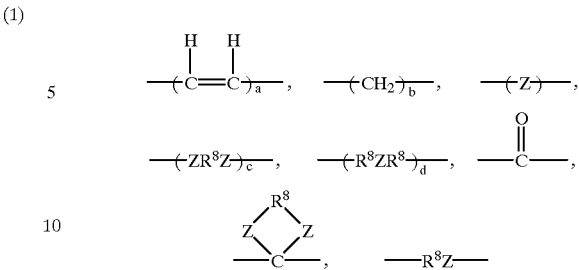

wherein Z is an oxygen atom or a sulfur atom, $R^8$ is an alkylene group with 1 to 6 carbon atoms, and a, b, c and d are, independently of each other, integers of from 1 to 4.

16. A chromene compound represented by the formula (5),

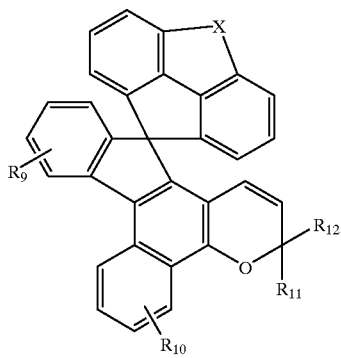

(5)

wherein, $R^9$ and $R^{10}$, independently of each other, represent, hydrogen atom, alkyl group, alkoxy group, aralkoxy group, substituted amino group, cyano group, substituted or unsubstituted aryl group, halogen atom, aralkyl group, substituted or unsubstituted heterocyclic group having a nitrogen atom as a hetero atom and bonded to the indene ring through the nitrogen atom, in the case of $R^9$, or to the naphthalene ring, in the case of $R^{10}$, or condensed heterocyclic group in which said heterocyclic group is condensed with an aromatic hydrocarbon ring or an aromatic heterocyclic ring;

$R^{11}$ and $R^{12}$, independently from each other, represent substituted or unsubstituted aryl group, or substituted or unsubstituted heteroaryl group; and X represents one of the following groups:

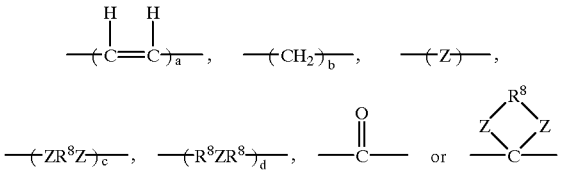

wherein Z is an oxygen atom or a sulfur atom, $R^8$ is an alkylene group with 1 to 6 carbon atoms, and a, b, c and d are, independently of each other, integers of from 1 to 4.

17. A photochromic material as set forth in claim 5, which further comprises an organic solvent for said chromene compound.

18. A photochromic material as set forth in claim 5, wherein said chromene compound is dispersed in a high-molecular weight solid material.

19. A chromene compound represented by the formula (1),

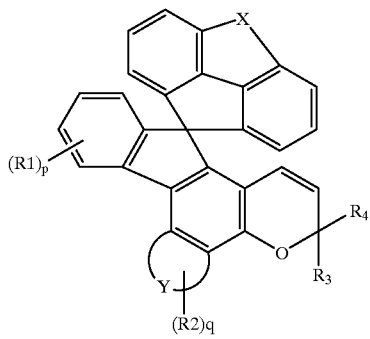

(1)

wherein,
R$^1$ is an alkyl group, a hydroxy group an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the indene ring through the carbon atom, a substituted or unsubstituted heterocyclic group having a nitrogen atom as a hetero atom and bonded to the indene ring through the nitrogen atom, or a monovalent condensed heterocyclic group in which said heterocyclic group is condensed with an aromatic hydrocarbon ring or an aromatic heterocyclic ring, and p is an integer of from 0 to 3;

a divalent group represented by the following formula (2),

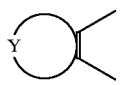

(2)

is an aromatic hydrocarbon group or an unsaturated heterocyclic ring;

R$^2$ is an alkyl group, a hydroxy group, an alkoxy group, an aralkoxy group, an amino group, a substituted amino group, a cyano group, a nitro group, a substituted or unsubstituted aryl group, a halogen atom, a trifluoromethyl group, an aralkyl group, a monovalent heterocyclic group bonded to the ring of the group represented by the above formula (2) through the carbon atom, a substituted or unsubstituted heterocyclic group having a nitrogen atom as a hetero atom and is bonded to the ring of the group represented by the above formula (2) through the nitrogen atom, or a monovalent condensed heterocyclic group in which said heterocyclic group is condensed with an aromatic hydrocarbon ring or an aromatic heterocyclic ring, q is an integer of from 0 to 3;

R$^3$ and R$^4$, independently from each other, represent a group of formula (3), formula (4), substituted or unsubstituted aryl group, or substituted or unsubstituted heteroaryl group;

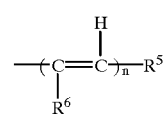

(3)

wherein R$^5$ is a substituted or unsubstituted aryl group, or a substituted or unsubstituted heteroaryl group, R$^6$ is a hydrogen atom, an alkyl group or a halogen atom, and n is an integer of from 1 to 3;

(4)

wherein R$^7$ is a substituted or unsubstituted aryl group, or a substituted or unsubstituted heteroaryl group, and m is an integer of from 1 to 3; or R$^3$ and R$^4$ are groups which, in combination, form an aliphatic hydrocarbon ring or an aromatic hydrocarbon ring; and X is represented by one of the following formula,

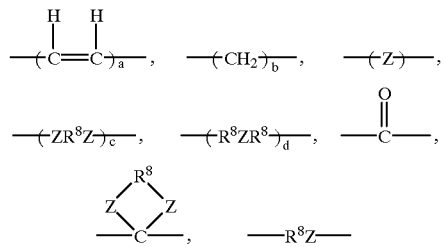

wherein Z is an oxygen atom or a sulfur atom, R$^8$ is an alkylene group with 1 to 6 carbon atoms, and a, b, c and d are, independently of each other, integers of from 1 to 4.

20. A photochromic material comprising a chromene compound of claim 19.

21. A photochromic optical material containing a chromene compound of claim 11.

22. A photochromic polymerizable composition containing a chromene compound of claim 19, and a polymerizable monomer.

23. A photochromic polymerizable composition according to claim 22, further comprising a polymerization initiator.

24. A photochromic polymerizable composition according to claim 23, wherein said polymerizable monomer comprises a (meth)acrylic acid ester compound.

25. A photochromic polymerizable composition according to claim 22, wherein said polymerizable monomer comprises a (meth)acrylic acid ester compound.

26. A chromene compound according to claim 19, wherein the group —R$^8$Z— is the group —CH$_2$O—.

* * * * *